United States Patent
Hunks et al.

(10) Patent No.: US 8,008,117 B2
(45) Date of Patent: Aug. 30, 2011

(54) ANTIMONY AND GERMANIUM COMPLEXES USEFUL FOR CVD/ALD OF METAL THIN FILMS

(75) Inventors: William Hunks, Waterbury, CT (US); Tianniu Chen, Rocky Hill, CT (US); Chongying Xu, New Milford, CT (US); Jeffrey F. Roeder, Brookfield, CT (US); Thomas H. Baum, New Fairfield, CT (US); Melissa A. Petruska, Newtown, CT (US); Matthias Stender, New Milford, CT (US); Philip S. H. Chen, Bethel, CT (US); Gregory T. Stauf, New Milford, CT (US); Bryan C. Hendrix, Danbury, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 12/860,906

(22) Filed: Aug. 22, 2010

(65) Prior Publication Data

US 2010/0317150 A1    Dec. 16, 2010

Related U.S. Application Data

(63) Continuation of application No. 12/307,101, filed as application No. PCT/US2007/063830 on Mar. 12, 2007, now Pat. No. 7,838,329.

(60) Provisional application No. 60/887,249, filed on Jan. 30, 2007, provisional application No. 60/864,073, filed on Nov. 2, 2006.

(51) Int. Cl.
    *H01L 21/06*    (2006.01)
(52) U.S. Cl. ................... 438/102; 438/95; 257/E21.101
(58) Field of Classification Search ........................ None
    See application file for complete search history.

(56) References Cited

U.S. PATENT DOCUMENTS

| | | | |
|---|---|---|---|
| 4,960,916 | A | 10/1990 | Pazik |
| 4,962,214 | A | 10/1990 | Villacorta et al. |
| 5,453,494 | A | 9/1995 | Kirlin et al. |
| 6,005,127 | A | 12/1999 | Todd et al. |
| 6,146,608 | A | 11/2000 | Todd et al. |
| 6,646,122 | B1 | 11/2003 | Nuhlen et al. |
| 6,787,186 | B1 | 9/2004 | Hintermaier |
| 6,872,963 | B2 | 3/2005 | Kostylev et al. |
| 6,984,591 | B1 | 1/2006 | Buchanan et al. |
| 6,998,289 | B2 | 2/2006 | Hudgens et al. |
| 7,029,978 | B2 | 4/2006 | Dodge |

(Continued)

FOREIGN PATENT DOCUMENTS

EP    1675194 A2    6/2006

(Continued)

OTHER PUBLICATIONS

Kim, R., et al., "Structural Properties of Ge2Sb2Te5 thin films by metal organic chemical vapor deposition for phase change memory...", "Applied Physics Letters", 2006, vol. 89, No. 102107.

(Continued)

*Primary Examiner* — Charles Garber
*Assistant Examiner* — Yasser A Abdelaziez
(74) *Attorney, Agent, or Firm* — Steven J. Hultquist; Hultquist IP; Maggie Chappuis

(57) ABSTRACT

Antimony, germanium and tellurium precursors useful for CVD/ALD of corresponding metal-containing thin films are described, along with compositions including such precursors, methods of making such precursors, and films and microelectronic device products manufactured using such precursors, as well as corresponding manufacturing methods. The precursors of the invention are useful for forming germanium-antimony-tellurium (GST) films and microelectronic device products, such as phase change memory devices, including such films.

20 Claims, 5 Drawing Sheets

U.S. PATENT DOCUMENTS

| | | | |
|---|---|---|---|
| 7,115,927 | B2 | 10/2006 | Hideki et al. |
| 7,312,165 | B2 | 12/2007 | Jursich et al. |
| 7,371,429 | B2 | 5/2008 | Lee et al. |
| 7,402,851 | B2 | 7/2008 | Hideki et al. |
| 7,425,735 | B2 | 9/2008 | Park et al. |
| 7,462,900 | B2 | 12/2008 | Hideki et al. |
| 7,476,917 | B2 | 1/2009 | Hideki et al. |
| 7,615,401 | B2 | 11/2009 | Park et al. |
| 7,704,787 | B2 | 4/2010 | Hideki et al. |
| 7,728,172 | B2 | 6/2010 | Lee et al. |
| 2002/0004266 | A1 | 1/2002 | Hashimoto et al. |
| 2002/0090815 | A1 | 7/2002 | Koike et al. |
| 2003/0135061 | A1 | 7/2003 | Norman et al. |
| 2004/0038808 | A1 | 2/2004 | Hampden-Smith et al. |
| 2004/0197945 | A1 | 10/2004 | Woelk et al. |
| 2004/0215030 | A1 | 10/2004 | Norman |
| 2005/0082624 | A1 | 4/2005 | Gousev et al. |
| 2005/0208699 | A1 | 9/2005 | Furkay et al. |
| 2005/0283012 | A1 | 12/2005 | Xu et al. |
| 2005/0287747 | A1 | 12/2005 | Chakravarti et al. |
| 2006/0006449 | A1 | 1/2006 | Jeong et al. |
| 2006/0027451 | A1 | 2/2006 | Park et al. |
| 2006/0049447 | A1 | 3/2006 | Lee et al. |
| 2006/0115595 | A1 | 6/2006 | Shenai-Khatkhate et al. |
| 2006/0138393 | A1 | 6/2006 | Seo et al. |
| 2006/0141155 | A1 | 6/2006 | Gordon et al. |
| 2006/0172067 | A1 | 8/2006 | Ovshinsky et al. |
| 2006/0172083 | A1 | 8/2006 | Lee et al. |
| 2006/0180811 | A1 | 8/2006 | Lee et al. |
| 2007/0154637 | A1 | 7/2007 | Shenai-Khatkhate et al. |
| 2007/0160760 | A1 | 7/2007 | Shin et al. |
| 2008/0254232 | A1 | 10/2008 | Gordon et al. |
| 2009/0215225 | A1 | 8/2009 | Stender et al. |
| 2009/0305458 | A1 | 12/2009 | Hunks et al. |

FOREIGN PATENT DOCUMENTS

| | | |
|---|---|---|
| JP | 58038296 A | 3/1983 |
| WO | 2004046417 A2 | 6/2004 |
| WO | 2006012052 A2 | 2/2006 |

OTHER PUBLICATIONS

Meller, A., et al., "Synthesis and Isolation of New Germanium (II) Compounds and of Free Germylenes", 1984, pp. 2020-2029, vol. 118 (English Abstract).

Anderson, Herbert H., "Dialkylaminogermanes and Dialkylaminosilanes", "J. Amer. Chem. Soc.", Mar. 20, 1952, pp. 1421-1423, vol. 74, No. 6.

Chorley, R. et al., "Subvalent Group 14 metal compounds. The X-ray crystal structures of two monomeric Group 14 metal bisamides, Ge[N(SiMe,).", "Inorganica Chemica Acta", 1992, pp. 203-209, Publisher: Elsevier.

Foley, S. et al., "Facile Formation of Rare Terminal Chalcogenido Germanium Complexes with Alkyllamidinates as Supporting Ligands", "J. Am. Chem", 1997, pp. 10359-10363, vol. 119.

Gupta, A. et al., "Triorganoantimony(V) complexes with internally functionallized oximes: synthetic, spectroscopic and structural aspects..", "Journal of Organometallic Chemistry", 2002, pp. 118-126, vol. 645.

Karsch, H. et al., "Bis(amidinate) Complexes of Silicon and Germanium", "Eur. J. Inorg. Chemistry", 1998, pp. 433-436.

Kim, S. et al., "Electrical Properties and Crystal Structures of Nitrogen Doped Ge2Sb2Te5 Thin Film for Phase Change Memory", "Thin Solid Films", Oct. 30, 2004, pp. 322-326, vol. 469-470.

Lappert, M. et al., "monomeric, coloured germanium (II) and tin (II) di-t-butylamides, and the crystal and molecular structure of Ge (NCMe2..", "J.C.S. Chem. Comm.", 1980, pp. 621-622.

Lee, J. et al., "GeSbTe deposition for the PRAM application", "Applied Surface Science", 2007, pp. 3969-3976, vol. 253, Publisher.

Mathur, S. et al., "Germanium Nanowires and Core-Shell Nanostructures by Chemical Vapor Deposition of [Ge (C5H5)2]", "Chem. Mater.", May 15, 2004, pp. 2449-2456, vol. 16.

Raj, P. et al., "Synthesis and characterization of the complex triorganoantimony (V) cations (CAPLUS Abstract; Accession No. 117:48764)", "Synthesis and Reactivity in Inorganic and Metal-organic Chemistry", 1992, pp. 543-557, vol. 22, No. 5 (Only Abstract Provided).

Raj, P. et al., "Synthesis and geometry of the complex triorganoantimony (V) cations (CAPLUS Abstract; Accession No. 118: 147667)", "Synthesis and Reactivity in Inorganic and Metal-organic Chemistry", 1992, pp. 1472-1494, vol. 22, No. 10 (Only Abstract Provided).

Veprek, S. et al., "Organometallic chemical vapor deposition of germanium from a cyclic germylene, 1,3-Di-tert-butyl-1,3,2-diazagermolidin..", "Chem. Mater.", 1996, pp. 825-831, vol. 8, Publisher: American Chemical Society.

Sb(NMe$_2$)$_3$: 9.92 mg WITH T$_{90}$ AT 98.5°C AND 1.5% MASS RESIDUAL;
Sb(NEtMe)$_3$: 6.67 mg WITH T$_{90}$ AT 131.8°C AND 0.2% MASS RESIDUAL

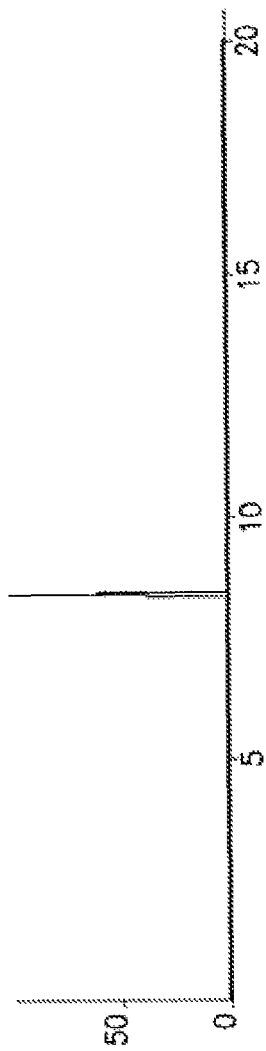
FIG.4a
| PKNO | R.TIME | I.TIME | F.TIME | A/H(sec) | AREA | HEIGHT | % TOTAL | NAME |
|---|---|---|---|---|---|---|---|---|
| 1 | 8.413 | 8.375 | 8.500 | 1.769 | 2040327 | 1153310 | 99.85 | |
| 2 | 8.585 | 8.575 | 8.608 | 1.117 | 3009 | 2693 | 0.15 | |
FIG.4b
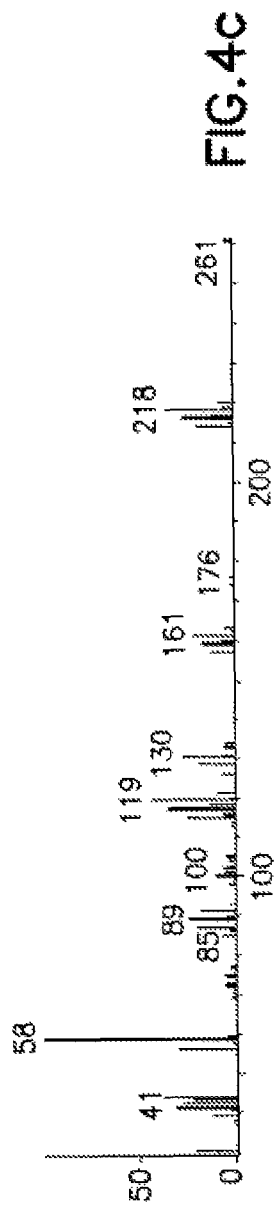
FIG.4c

ANTIMONY AND GERMANIUM COMPLEXES USEFUL FOR CVD/ALD OF METAL THIN FILMS

CROSS-REFERENCE TO RELATED APPLICATIONS

This is a continuation of U.S. patent application Ser. No. 12/307,101 filed Feb. 20, 2009, and issued as U.S. Pat. No. 7,838,329 on Nov. 23, 2010, which in turn is a U.S. national phase under the provisions of 35 USC §371 of International Application No. PCT/US07/63830 filed Mar. 12, 2007, which in turn claims the benefit of priority under 35 USC §119 of U.S. Provisional Patent Application No. 60/864,073 filed Nov. 2, 2006, and the benefit of priority under 35 USC §119 of U.S. Provisional Patent Application No. 60/887,249 filed Jan. 30, 2007. The disclosures of all such applications and/or patents are hereby incorporated herein by reference in their respective entireties, for all purposes.

FIELD OF THE INVENTION

The present invention relates to antimony and germanium complexes useful for CVD/ALD of metal thin films, to compositions including such complexes and to processes for depositing metal films on substrates using such complexes and compositions.

DESCRIPTION OF THE RELATED ART

Antimonides have been utilized in infrared detectors, high-speed digital circuits, quantum well structures and recently as a critical component together with germanium (Ge) and tellurium (Te) in phase change chalcogenide nonvolatile memory technology utilizing germanium-antimony-tellurium ($Ge_2Sb_2Te_5$) films.

Phase-change random access memory (PRAM) devices based on Ge—Sb—Te (GST) thin films utilize a reversible transition from a crystalline state to an amorphous state associated with changes in resistivity of the film material. The film material itself for high-speed commercial manufacturing and performance reasons is desirably formed using techniques such as chemical vapor deposition (CVD) and atomic layer deposition (ALD).

Despite their promise, there are substantial challenges facing the efforts being made to grow reproducible, high-quality antimonide, $Sb_2Te_3$ and GST films by CVD and atomic layer deposition ALD at low temperature. These challenges include the following:

(1) a very limited number of antimony CVD/ALD precursors is currently available, most being alkyl-based compounds such as $Me_3Sb$, $Et_3Sb$, $(iPr)_3Sb$ and $Ph_3Sb$ or hydride-based compounds such as $SbH_3$, and these precursors suffer from various deficiencies including low thermal stability, low volatility, synthetic difficulties and high delivery temperatures;

(2) the compatibility of such currently available antimony precursors with germanium or tellurium precursors is undetermined as far as their ability to reproducibly grow microelectronic device quality GST films, and the growth of antimonide films has associated process difficulties, including sensitivity to the V/III ratio and decomposition temperature; and (3) the deposited metal films formed from such precursors are susceptible to carbon or heteroatom contamination deriving from the precursor that can result in low growth rates, poor morphology and compositional variations in the films.

Similar issues are encountered in the availability and selection of suitable germanium precursors for deposition of GST films, and in the use of germanium precursors for forming epitaxially grown strained silicon films, e.g., SiGe films.

Germane (GeH4) is conventionally used to form germanium films but requires deposition temperatures above 500° C. as well as rigorous safety controls and equipment. Other available Ge precursors require temperatures above 350° C. for deposition of Ge films, or otherwise exhibit insufficient vapor pressures for transport or produce low film growth rates. Ideally, the germanium precursor can be used in CVD/ALD processes at low temperatures, on the order of 300° C. and below, to form GST alloy thin films at high deposition rates, and with low carbon impurity levels in the resulting films.

In consequence, the art continues to seek new antimony and germanium precursors for use in deposition of corresponding metal and metal alloy films by CVD and ALD techniques.

SUMMARY OF THE INVENTION

The present invention relates to antimony and germanium precursors useful for CVD/ALD of corresponding metal-containing thin films, to compositions including such precursors, methods of making such precursors, and films and microelectronic device products manufactured using such precursors, as well as corresponding manufacturing methods.

In one aspect, the invention relates to a metal complex selected from among complexes of formulae (A), (B), (C), (D) and (E)(I)-(E)(XVI):

$$Sb(NR^1R^2)(R^3N(CR^5R^6)_mNR^4) \quad (A)$$

wherein:
$R^1$, $R^2$, $R^3$, and $R^4$ may be the same as or different from one another, and are independently selected from $C_1$-$C_6$ alkyl, $C_3$-$C_6$ cycloalkyl, $C_2$-$C_6$ alkenyl (e.g., vinyl, allyl, etc.), $C_3$-$C_6$ alkylsilyl, $C_6$-$C_{10}$ aryl,
each of $R^5$ and $R^6$ may be the same as or different from one another and are independently selected from hydrogen, $C_1$-$C_6$ alkyl, $C_3$-$C_6$ cycloalkyl, $C_2$-$C_6$ alkenyl (e.g., vinyl, allyl, etc.), $C_3$-$C_6$ alkylsilyl, and $C_6$-$C_{10}$ aryl; and
m is an integer from 1 to 4 inclusive;

$$Sb(R^1)(R^2N(CR^4R^5)_mNR^3) \quad (B)$$

wherein:
$R^1$, $R^2$, and $R^3$ may be the same as or different from one another, and are independently selected from $C_1$-$C_6$ alkyl, $C_3$-$C_6$ cycloalkyl, $C_2$-$C_6$ alkenyl (e.g., vinyl, allyl, etc.), $C_3$-$C_6$ alkylsilyl, and $C_6$-$C_{10}$ aryl;
each of $R^4$ and $R^5$ may be the same as or different from one another and is independently selected from hydrogen, $C_1$-$C_6$ alkyl, $C_3$-$C_6$ cycloalkyl, $C_2$-$C_6$ alkenyl (e.g., vinyl, allyl, etc.), $C_3$-$C_6$ alkylsilyl, and $C_6$-$C_{10}$ aryl; and
m is an integer from 1 to 4 inclusive;

$$Sb(R^1)_{3-n}(NR^2R^3)_n \quad (C)$$

wherein:
$R^1$, $R^2$ and $R^3$ may be the same as or different from one another and are independently selected from hydrogen, $C_1$-$C_6$ alkyl, $C_3$-$C_6$ cycloalkyl, $C_2$-$C_6$ alkenyl (e.g., vinyl, allyl, etc.), silyl, $C_3$-$C_6$ alkylsilyl, $C_6$-$C_{10}$ aryl and —$NR^4R^5$, wherein each of $R^4$ and $R^5$ is selected from among H and $C_1$-$C_4$; and
n is an integer from 0 to 3 inclusive;

$$(R^4)_nSb(E(R^1R^2R^3))_{3-n} \quad (D)$$

wherein:

$R^1$, $R^2$, $R^3$, and $R^4$ may be the same as or different from one another, and are independently selected from $C_1$-$C_6$ alkyl, $C_3$-$C_6$ cycloalkyl, $C_3$-$C_6$ alylsilyl, $C_6$-$C_{10}$ aryl, and alkylamino of the formula —$NR^5R^6$ wherein each of $R^5$ and $R^6$ is independently selected from H and $C_1$-$C_4$ alkyl;

E is silicon (Si) or germanium (Ge); and n is an integer from 0 to 3 inclusive;

(E) germanium precursors of the following formulae I-XVI:

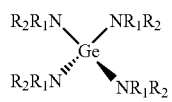

I wherein:

$R_1$ and $R_2$ may be the same as or different from one another, and are independently selected from H, $C_1$-$C_6$ alkyl, $C_2$-$C_5$ alkenyl, $C_5$-$C_{10}$ cycloalkyl, $C_6$-$C_{10}$ aryl, and —$Si(R_3)_3$ wherein each $R_3$ is independently selected from $C_1$-$C_6$ alkyl;

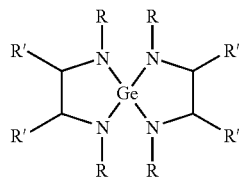

II wherein:

R and R' may be the same as or different from one another, and each R and R' is independently selected from H, $C_1$-$C_6$ alkyl, $C_2$-$C_5$ alkenyl, $C_5$-$C_{10}$ cycloalkyl, $C_6$-$C_{10}$ aryl, and —$Si(R_3)_3$ wherein each $R_3$ is independently selected from $C_1$-$C_6$ alkyl;

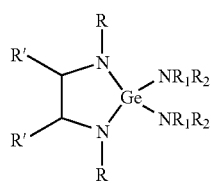

III wherein:

R, R', $R_1$ and $R_2$ may be the same as or different from one another, and each is independently selected from H, $C_1$-$C_6$ alkyl, $C_2$-$C_5$ alkenyl, $C_5$-$C_{10}$ cycloalkyl, $C_6$-$C_{10}$ aryl, and —$Si(R_3)_3$ wherein each $R_3$ is independently selected from $C_1$-$C_6$ alkyl;

IV wherein:

R, $R_1$ and $R_2$ may be the same as or different from one another, and each is independently selected from H, $C_1$-$C_6$ alkyl, $C_2$-$C_5$ alkenyl, $C_5$-$C_{10}$ cycloalkyl, $C_6$-$C_{10}$ aryl, and —$Si(R_3)_3$ wherein each $R_3$ is independently selected from $C_1$-$C_6$ alkyl; and n is an integer from 0 to 4 inclusive;

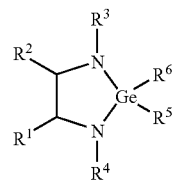

V wherein:

$R^1$, $R^2$, $R^3$, $R^4$, $R^5$ and $R^6$ may be the same as or different from one another, and each is independently selected from H, $C_1$-$C_6$ alkyl, $C_2$-$C_5$ alkenyl, $C_5$-$C_{10}$ cycloalkyl, $C_6$-$C_{10}$ aryl, and —$Si(R_3)_3$ wherein each $R_3$ is independently selected from $C_1$-$C_6$ alkyl;

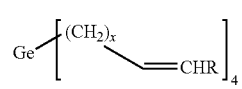

VI wherein:

R is selected from H, $C_1$-$C_6$ alkyl, and $C_6$-$C_{10}$ aryl; and x is 0, 1 or 2;

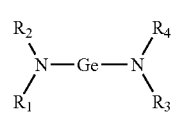

VII wherein:

$R_1$, $R_2$, $R_3$ and $R_4$ may be the same as or different from the others, and each is independently selected from among H, $C_1$-$C_6$ alkyl, $C_5$-$C_{10}$ cycloalkyl, $C_6$-$C_{10}$ aryl, and —$Si(R_3)_3$ wherein each $R_3$ is independently selected from $C_1$-$C_6$ alkyl;

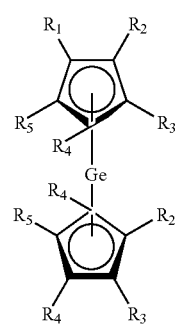

VIII wherein:

$R_1$, $R_2$, $R_3$, $R_4$, and $R_5$ may be the same as or different from one another, and each is independently selected from among H, $C_1$-$C_6$ alkyl, silyl, —$Si(R')_3$, $C_6$-$C_{10}$ cycloalkyl, $C_6$-$C_{10}$ aryl, —$(CH_2)_xNR'R''$, and —$(CH_2)_xOR'''$, wherein x=1, 2 or 3, and R', R'' and R''' may be the same as or different from one another, and each is independently selected from $C_1$-$C_6$ alkyl;

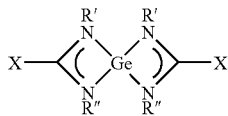

IX wherein:
R' and R" may be the same as or different from one another, and are independently selected from among H, $C_1$-$C_6$ alkyl, $C_5$-$C_{10}$ cycloalkyl, $C_6$-$C_{10}$ aryl, and —Si($R^3$)$_3$ wherein each $R^3$ is independently selected from $C_1$-$C_6$ alkyl; and
each X is independently selected from among $C_1$-$C_6$ alkyl, $C_1$-$C_6$ alkoxy, —NR$^1$R$^2$, and —C($R^3$)$_3$, wherein each of $R^2$ and $R^3$ is independently selected from H, $C_1$-$C_6$ alkyl, $C_5$-$C_{10}$ cycloalkyl, $C_6$-$C_{10}$ aryl, and —Si($R^4$)$_3$ wherein each $R^4$ is independently selected from $C_1$-$C_6$ alkyl;

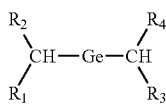

X wherein:
$R_1$, $R_2$, $R_3$ and $R_4$ may be same as or different from one another, and are independently selected from among H, $C_1$-$C_6$ alkyl, $C_5$-$C_{10}$ cycloalkyl, $C_6$-$C_{10}$ aryl, and —Si($R^3$)$_3$ wherein each $R^3$ is independently selected from $C_1$-$C_6$ alkyl;

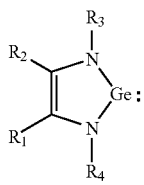

XI wherein:
$R_1$, $R_2$, $R_3$ and $R_4$ may be the same as or different from one another, and are independently selected from among H, $C_1$-$C_6$ alkyl, $C_5$-$C_{10}$ cycloalkyl, $C_6$-$C_{10}$ aryl, and —Si($R^3$)$_3$ wherein each $R^3$ is independently selected from $C_1$-$C_6$ alkyl;

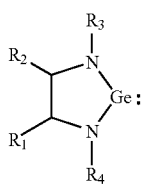

XII wherein:
$R_1$, $R_2$, $R_3$ and $R_4$ may be the same as or different from one another, and are independently selected from among H, $C_1$-$C_6$ alkyl, $C_5$-$C_{10}$ cycloalkyl, $C_6$-$C_{10}$ aryl, and —Si($R^3$)$_3$ wherein each $R^3$ is independently selected from $C_1$-$C_6$ alkyl;

$R_1TeR_2$      XIII wherein:
$R_1$ and $R_2$ may be the same as or different from one another, and are independently selected from among H, $C_1$-$C_6$ alkyl, $C_5$-$C_{10}$ cycloalkyl, $C_6$-$C_{10}$ aryl, and —Si($R^3$)$_3$ wherein each $R^3$ is independently selected from $C_1$-$C_6$ alkyl;

$R_1Te(NR_2R_3)$      XIV wherein:
$R_1$, $R_2$ and $R_3$ may be the same as or different from one another, and are independently selected from among H, $C_1$-$C_6$ alkyl, $C_5$-$C_{10}$ cycloalkyl, $C_6$-$C_{10}$ aryl, and —Si($R_3$)$_3$ wherein each $R_3$ is independently selected from $C_1$-$C_6$ alkyl;

$R_1Te$—$TeR_2$      XV wherein:
$R_1$ and $R_2$ may be the same as or different from one another, and are independently selected from among H, $C_1$-$C_6$ alkyl, $C_5$-$C_{10}$ cycloalkyl, $C_6$-$C_{10}$ aryl, and —Si($R^3$)$_3$ wherein each $R^3$ is independently selected from $C_1$-$C_6$ alkyl; and $R_1R_2R_3R_4Ge$      XVI wherein:
$R_1$, $R_2$, $R_3$, and $R_4$ may be the same as or different from one another, and are independently selected from among H, $C_1$-$C_6$ alkyl, $C_5$-$C_{10}$ cycloalkyl, $C_6$-$C_{10}$ aryl, and —Si($R^3$)$_3$ wherein each $R^3$ is independently selected from $C_1$-$C_6$ alkyl.

In another aspect, the invention relates to a vapor of an above-described metal complex.

In another aspect, the invention relates to a precursor mixture including germanium precursor, antimony precursor and tellurium precursor, wherein at least one of the germanium precursor and antimony precursor includes a precursor selected from among the metal complexes of formulae (A), (B), (C), (D) and (E)(I)-(XVI) above.

In a further aspect, the invention relates to precursor composition comprising a metal complex of the invention, in a solvent medium.

A further aspect of the invention relates to method of depositing metal on a substrate, comprising contacting the substrate with precursor vapor comprising vapor of a metal complex of the invention.

Additional aspects of the invention relate to methods of making the precursors of the invention.

A further aspect of the invention relates to $Sb(NMeEt)_3$, $Sb(CH=CMe_2)_3$ and $Sb(CH_2CH=CH_2)_3$.

In another aspect, the invention relates to a packaged precursor supply system comprising a package containing a metal complex of the invention.

Yet another aspect of the invention relates to a germanium complex whose structure and properties are more fully discussed hereinafter.

In another aspect, the invention relates to a method of depositing germanium on a substrate, comprising contacting the substrate with precursor vapor comprising vapor of a germanium (II) complex selected from among the following:

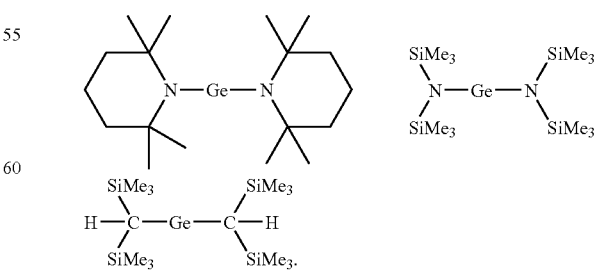

Another aspect of the invention relates to a method of method of depositing germanium on a substrate, comprising contacting the substrate with precursor vapor comprising vapor of dialkylaminotriisopropylgermane.

The invention also contemplates a precursor vapor comprising vapor of dialkylaminotriisopropylgermane, in another aspect of the invention.

One aspect of the invention relates to a method of depositing germanium on a substrate, comprising contacting the substrate with a precursor vapor comprising vapor of a germanium complex including ligands selected from among allyl, benzyl, t-butyl, cylopentadienyl, hydride, phenyl, alkyl, bidentate amines and N,N-dialkylethylenediamine.

Another aspect of the invention relates to forming a GST film on a substrate, comprising contacting the substrate with a precursor vapor comprising vapor of a germanium complex of the invention, vapor of an antimony complex, and vapor of a tellurium complex.

Another aspect of the invention relates to a dialkylaminotriisopropylgermane complex, e.g., diethylaminotriisopropylgermane and ethylmethylaminotriisopropylgermane.

A still further aspect of the invention relates to a method of forming a germanium-containing film on a substrate, comprising contacting the substrate with a precursor vapor comprising vapor of diethylaminotriisopropylgermane or ethylmethylaminotriisopropylgermane.

A still further aspect of the invention relates to a method of making a microelectronic device, comprising chemical vapor deposition or atomic layer deposition of a metal-containing film on a substrate from a precursor vapor comprising vapor of at least one precursor as described herein.

Where a range of carbon numbers is provided herein, in description of a corresponding chemical moiety, it is understood that each intervening carbon number and any other stated or intervening carbon number value in that stated range, is encompassed within the invention, e.g., $C_1$-$C_6$ alkyl is understood as including methyl($C_1$), ethyl($C_2$), propyl($C_3$), butyl ($C_4$), pentyl($C_5$) and hexyl($C_6$), and the chemical moiety may be of any conformation, e.g., straight-chain or branched, it being further understood that sub-ranges of carbon number within specified carbon number ranges may independently be included in smaller carbon number ranges, within the scope of the invention, and that ranges of carbon numbers specifically excluding a carbon number or numbers are included in the invention, and sub-ranges excluding either or both of carbon number limits of specified ranges are also included in the invention.

As used herein, the term "film" refers to a layer of deposited material having a thickness below 1000 micrometers, e.g., from such value down to atomic monolayer thickness values. In various embodiments, film thicknesses of deposited material layers in the practice of the invention may for example be below 100, 10, or 1 micrometers, or in various thin film regimes below 200, 100, or 50 nanometers, depending on the specific application involved.

It is noted that as used herein and in the appended claims, the singular forms "a", "and", and "the" include plural referents unless the context clearly dictates otherwise.

Other aspects, features and embodiments of the invention will be more fully apparent from the ensuing disclosure and appended claims.

BRIEF DESCRIPTION OF THE DRAWINGS

FIG. 4(a) is a gas chromatography (GC) spectrum for such ethylmethylaminotriisopropylgermane product, and FIG. 4(b) is a corresponding tabulation of peak data for such GC spectrum. FIG. 4(c) is a mass spectrum for the ethylmethylaminotriisopropylgermane product.

DETAILED DESCRIPTION OF THE INVENTION, AND PREFERRED EMBODIMENTS THEREOF

Figure 1:
FIG. 1 shows the nuclear magnetic resonance spectrum of Sb(NMeEt)$_3$.

The present invention relates to antimony and germanium precursors useful for CVD/ALD of corresponding metal-containing thin films, to compositions including such precursors, methods of making such precursors, and films and microelectronic device products manufactured using such precursors, as well as corresponding manufacturing methods.

The invention relates in one aspect to new classes of antimony precursors, of the following formulae (A), (B) and (C):

$$Sb(NR^1R^2)(R^3N(CR^5R^6)_m NR^4) \quad (A)$$

wherein:
$R^1$, $R^2$, $R^3$, and $R^4$ may be the same as or different from one another, and are independently selected from $C_1$-$C_6$ alkyl, $C_3$-$C_6$ cycloalkyl, $C_2$-$C_6$ alkenyl (e.g., vinyl, allyl, etc.), $C_3$-$C_6$ alkylsilyl, $C_6$-$C_{10}$ aryl,
each of $R^5$ and $R^6$ may be the same as or different from one another and are independently selected from hydrogen, $C_1$-$C_6$ alkyl, $C_3$-$C_6$ cycloalkyl, $C_2$-$C_6$ alkenyl (e.g., vinyl, allyl, etc.), $C_3$-$C_6$ alkylsilyl, and $C_6$-$C_{10}$ aryl; and
m is an integer from 1 to 4 inclusive;

$$Sb(R^1)(R^2N(CR^4R^5)_m NR^3) \quad (B)$$

wherein:
$R^1$, $R^2$, and $R^3$ may be the same as or different from one another, and are independently selected from $C_1$-$C_6$ alkyl, $C_3$-$C_6$ cycloalkyl, $C_2$-$C_6$ alkenyl (e.g., vinyl, allyl, etc.), $C_3$-$C_6$ alkylsilyl, and $C_6$-$C_{10}$ aryl;
each of $R^4$ and $R^5$ may be the same as or different from one another and is independently selected from hydrogen, $C_1$-$C_6$ alkyl, $C_3$-$C_6$ cycloalkyl, $C_2$-$C_6$ alkenyl (e.g., vinyl, allyl, etc.), $C_3$-$C_6$ alkylsilyl, and $C_6$-$C_{10}$ aryl; and
m is an integer from 1 to 4 inclusive;

$$Sb(R^1)_{3-n}(NR^2R^3)_n \quad (C)$$

wherein:
$R^1$, $R^2$ and $R^3$ may be the same as or different from one another and are independently selected from hydrogen, $C_1$-$C_6$ alkyl, $C_3$-$C_6$ cycloalkyl, $C_2$-$C_6$ alkenyl (e.g., vinyl, allyl, etc.), silyl, $C_3$-$C_6$ alkylsilyl, $C_6$-$C_{10}$ aryl and —NR$^4$R$^5$, wherein each of $R^4$ and $R^5$ is selected from among H and $C_1$-$C_4$; and n is an integer from 0 to 3 inclusive.

The invention in another aspect relates to germanyl and silyl antimony precursors of formula (D):

$$(R^4)_n Sb(E(R^1R^2R^3))_{3-n} \quad (D)$$

wherein:

$R^1$, $R^2$, $R^3$, and $R^4$ may be the same as or different from one another, and are independently selected from $C_1$-$C_6$ alkyl, $C_3$-$C_6$ cycloalkyl, $C_3$-$C_6$ alylsilyl, $C_6$-$C_{10}$ aryl, and alkylamino of the formula —$NR^5R^6$ wherein each of $R^5$ and $R^6$ is independently selected from H and $C_1$-$C_4$ alkyl;

E is silicon (Si) or germanium (Ge); and n is an integer from 0 to 3 inclusive.

The foregoing precursors may be usefully employed for CVD and ALD of Sb, Sb/Ge, Sb/Te and GST films.

Such precursors may also be used in low temperature deposition applications with reducing co-reactants such as hydrogen, hydrogen plasma, amines, imines, hydrazines, silanes, silyl chalcogenides (e.g., $(Me_3Si)_2Te$), germanes (e.g., $GeH_4$), ammonia, alkanes, alkenes and alkynes.

When specific precursors are in a liquid state, they may be used for liquid delivery in neat liquid form.

Alternatively, when such precursors are in a liquid or solid state, they may be employed in suitable solvents, as a solution or suspension of the precursor. In specific applications, suitable solvents for such purpose include alkanes (e.g., hexane, heptane, octane and pentane), aryl solvents (e.g., benzene, toluene), amines (e.g., triethylamine, tert-butylamine), imines, hydrazines and ethers.

The choice of a specific solvent composition for a particular antimony precursor or for a specific antimony precursor in combination with other germanium and tellurium precursors, may be readily determined, within the skill of the art based on the disclosure herein, to select an appropriate single component or multiple component solvent medium for liquid delivery vaporization and transport of the specific precursor component(s) involved.

In various embodiments, where the antimony precursor is in a solid state, a solid delivery system may be utilized for delivery of the antimony precursor, such as for example the ProE-Vap® solid delivery and vaporizer system commercially available from ATMI, Inc., Danbury, Conn., USA.

The antimony precursors of the invention can be "fine-tuned" by choice of appropriate substituents, within the broad formulae set out hereinabove, to provide desired characteristics of thermal stability, volatility and compatibility with other co-reagents or components in a multi-component precursor system.

The antimony precursors of the invention are readily synthesized, by synthetic routes including those described below.

The antimony precursor of the general formula (A):

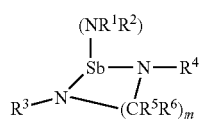

can for example be synthesized according to the following reaction scheme (A):

$$SbX_3 + Li(NR^1R^2) + Li(R^3N(CR^5R^6)_m NR^4) \longrightarrow$$

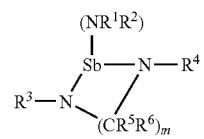

and the antimony precursor of the general formula (B):

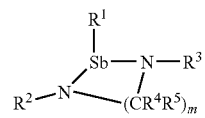

can be synthesized according to the following reaction scheme (B):

$$SbX_3 + R^1MgX + Li(R^2N(CR^4R^5)_m NR^3) \longrightarrow$$

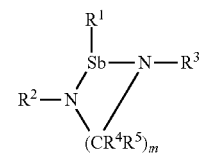

or by the following reaction scheme (C):

$$SbX_3 + mR^2(CR^4R^5) R^3NSiMe_3 \longrightarrow$$

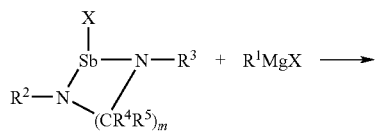

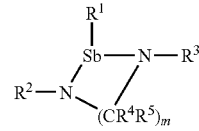

The antimony precursor of the general formula (C) can be formed by synthesis in a corresponding manner.

The antimony precursor of the general formula (D), having the following structure:

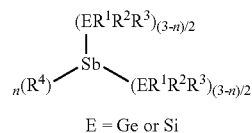

E = Ge or Si can for example be synthesized according to the following reaction schemes (D), when n is zero, or (E), when n is 2:

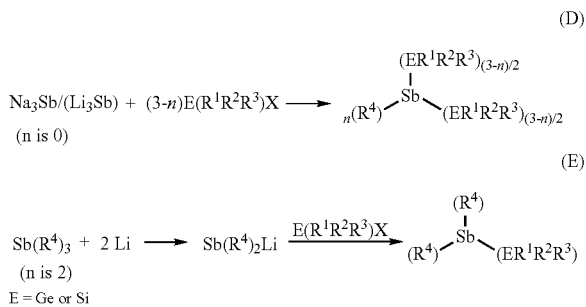

(D)

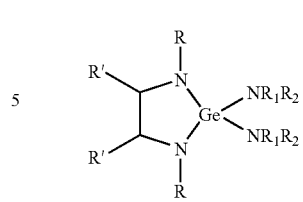

III wherein X is halo (fluorine, bromine, chlorine, iodine).

In the foregoing synthetic examples, RMgX and RLi can be used as alternative synthesis reagents.

As specific examples illustrative of precursors of the invention, the precursors $Sb(NMeEt)_3$, $Sb(CH=CMe_2)_3$, $Sb(CH_2CH=CH_2)_3$ and $Sb(NMe_2)_3$ were synthesized and characterized. The precursors $Sb(NMe_2)_3$ and $Sb(NMeEt)_3$ were determined to exhibit photo-sensitivity and therefore to require storage in a container protected from light exposure or in other photo-resistant packaging, to avoid light-induced decomposition thereof. Similar considerations are applicable to $Sb(CH=CMe_2)_3$ and $Sb(CH_2CH=CH_2)_3$.

Figure 2:
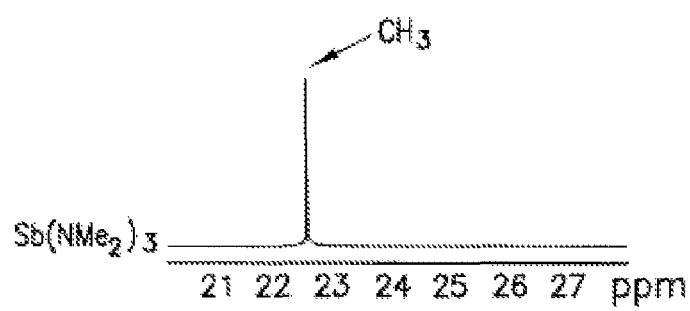
FIG. 2 shows the nuclear magnetic resonance spectrum of Sb(NMe$_2$)$_3$.

FIG. 1 shows the nuclear magnetic resonance spectrum of $Sb(NMeEt)_3$ and FIG. 2 shows the nuclear magnetic resonance spectrum of $Sb(NMe_2)_3$.

Figure 3:
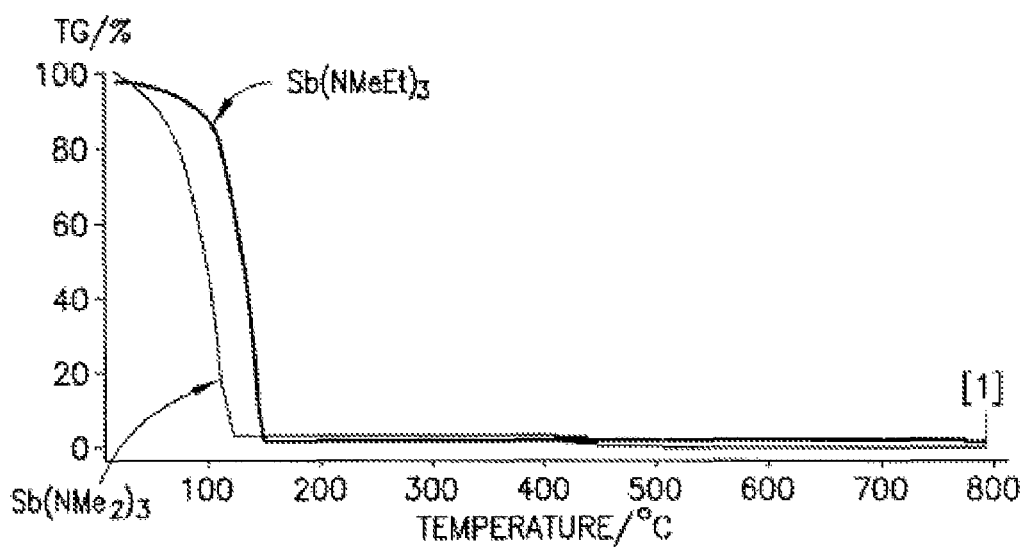
FIG. 3 is a simultaneous thermal analysis (STA) graph for Sb(NMeEt)$_3$ and Sb(NMe$_2$)$_3$, in which percentage thermogravimetry (TG) is plotted as a function of temperature, in degrees Centigrade.

FIG. 3 is a simultaneous thermal analysis (STA) graph for these two precursors, $Sb(NMeEt)_3$ and $Sb(NMe_2)_3$, in which percentage thermogravimetry (TG) is plotted as a function of temperature, in degrees Centigrade.

The invention in another aspect relates to germanium precursors useful for CVD and ALD deposition of germanium films on substrates, of the following formulae I-XVI:

I wherein:

$R_1$ and $R_2$ may be the same as or different from one another, and are independently selected from H, $C_1$-$C_6$ alkyl, $C_2$-$C_5$ alkenyl, $C_5$-$C_{10}$ cycloalkyl, $C_6$-$C_{10}$ aryl, and —$Si(R_3)_3$ wherein each $R_3$ is independently selected from $C_1$-$C_6$ alkyl;

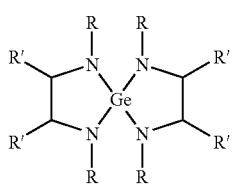

II wherein:

R and R' may be the same as or different from one another, and each R and R' is independently selected from H, $C_1$-$C_6$ alkyl, $C_2$-$C_5$ alkenyl, $C_5$-$C_{10}$ cycloalkyl, $C_6$-$C_{10}$ aryl, and —$Si(R_3)_3$ wherein each $R_3$ is independently selected from $C_1$-$C_6$ alkyl;

wherein:

R, R', $R_1$ and $R_2$ may be the same as or different from one another, and each is independently selected from H, $C_1$-$C_6$ alkyl, $C_2$-$C_5$ alkenyl, $C_5$-$C_{10}$ cycloalkyl, $C_6$-$C_{10}$ aryl, and —$Si(R_3)_3$ wherein each $R_3$ is independently selected from $C_1$-$C_6$ alkyl;

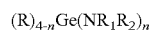

IV wherein:

R, $R_1$ and $R_2$ may be the same as or different from one another, and each is independently selected from H, $C_1$-$C_6$ alkyl, $C_2$-$C_5$ alkenyl, $C_5$-$C_{10}$ cycloalkyl, $C_6$-$C_{10}$ aryl, and —$Si(R_3)_3$ wherein each $R_3$ is independently selected from $C_1$-$C_6$ alkyl; and n is an integer from 0 to 4 inclusive;

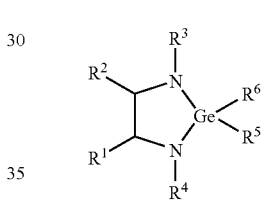

V wherein:

$R^1$, $R^2$, $R^3$, $R^4$, $R^5$ and $R^6$ may be the same as or different from one another, and each is independently selected from H, $C_1$-$C_6$ alkyl, $C_2$-$C_5$ alkenyl, $C_5$-$C_{10}$ cycloalkyl, $C_6$-$C_{10}$ aryl, and —$Si(R_3)_3$ wherein each $R_3$ is independently selected from $C_1$-$C_6$ alkyl;

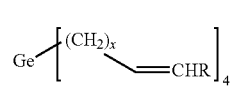

VI wherein:

R is selected from H, $C_1$-$C_6$ alkyl, and $C_6$-$C_{10}$ aryl; and x is 0, 1 or 2;

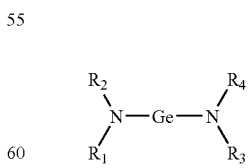

VII wherein:

$R_1$, $R_2$, $R_3$ and $R_4$ may be the same as or different from the others, and each is independently selected from among H, $C_1$-$C_6$ alkyl, $C_5$-$C_{10}$ cycloalkyl, $C_6$-$C_{10}$ aryl, and —$Si(R_3)_3$ wherein each $R_3$ is independently selected from $C_1$-$C_6$ alkyl;

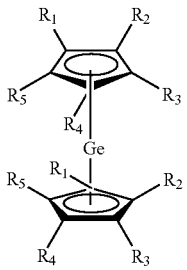

VIII wherein:
$R_1$, $R_2$, $R_3$, $R_4$, and $R_5$ may be the same as or different from one another, and each is independently selected from among H, $C_1$-$C_6$ alkyl, silyl, —Si(R')$_3$, $C_6$-$C_{10}$ cycloalkyl, $C_6$-$C_{10}$ aryl, —(CH$_2$)$_x$NR'R'', and —(CH$_2$)$_x$OR''', wherein x=1, 2 or 3, and R', R'' and R''' may be the same as or different from one another, and each is independently selected from $C_1$-$C_6$ alkyl;

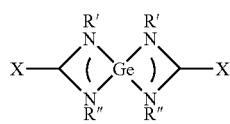

IX wherein:
R' and R'' may be the same as or different from one another, and are independently selected from among H, $C_1$-$C_6$ alkyl, $C_5$-$C_{10}$ cycloalkyl, $C_6$-$C_{10}$ aryl, and —Si(R$^3$)$_3$ wherein each R$^3$ is independently selected from $C_1$-$C_6$ alkyl; and
each X is independently selected from among $C_1$-$C_6$ alkyl, $C_1$-$C_6$ alkoxy, —NR$^1$R$^2$, and —C(R$^3$)$_3$, wherein each of R$^1$, R$^2$ and R$^3$ is independently selected from H, $C_1$-$C_6$ alkyl, $C_5$-$C_{10}$ cycloalkyl, $C_6$-$C_{10}$ aryl, and —Si(R$^4$)$_3$ wherein each R$^4$ is independently selected from $C_1$-$C_6$ alkyl;

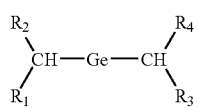

X wherein:
$R_1$, $R_2$, $R_3$ and $R_4$ may be same as or different from one another, and are independently selected from among H, $C_1$-$C_6$ alkyl, $C_5$-$C_{10}$ cycloalkyl, $C_6$-$C_{10}$ aryl, and —Si(R$^3$)$_3$ wherein each R$^3$ is independently selected from $C_1$-$C_6$ alkyl;

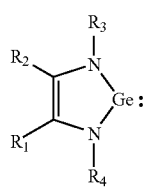

XI wherein:
$R_1$, $R_2$, $R_3$ and $R_4$ may be the same as or different from one another, and are independently selected from among H, $C_1$-$C_6$ alkyl, $C_5$-$C_{10}$ cycloalkyl, $C_6$-$C_{10}$ aryl, and —Si(R$^3$)$_3$ wherein each R$^3$ is independently selected from $C_1$-$C_6$ alkyl;

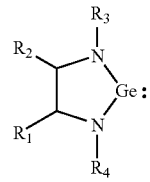

XII wherein:
$R_1$, $R_2$, $R_3$ and $R_4$ may be the same as or different from one another, and are independently selected from among H, $C_1$-$C_6$ alkyl, $C_5$-$C_{10}$ cycloalkyl, $C_6$-$C_{10}$ aryl, and —Si(R$^3$)$_3$ wherein each R$^3$ is independently selected from $C_1$-$C_6$ alkyl;

R$_1$TeR$_2$  XIII wherein:
$R_1$ and $R_2$ may be the same as or different from one another, and are independently selected from among H, $C_1$-$C_6$ alkyl, $C_5$-$C_{10}$ cycloalkyl, $C_6$-$C_{10}$ aryl, and —Si(R$^3$)$_3$ wherein each R$^3$ is independently selected from $C_1$-$C_6$ alkyl;

R$_1$Te(NR$_2$R$_3$)  XIV wherein:
$R_1$, $R_2$ and $R_3$ may be the same as or different from one another, and are independently selected from among H, $C_1$-$C_6$ alkyl, $C_5$-$C_{10}$ cycloalkyl, $C_6$-$C_{10}$ aryl, and —Si(R$_3$)$_3$ wherein each R$_3$ is independently selected from $C_1$-$C_6$ alkyl;

R$_1$Te—TeR$_2$  XV wherein:
$R_1$ and $R_2$ may be the same as or different from one another, and are independently selected from among H, $C_1$-$C_6$ alkyl, $C_5$-$C_{10}$ cycloalkyl, $C_6$-$C_{10}$ aryl, and —Si(R$^3$)$_3$ wherein each R$^3$ is independently selected from $C_1$-$C_6$ alkyl; and R$_1$R$_2$R$_3$R$_4$Ge  XVI wherein:
$R_1$, $R_2$, $R_3$, and $R_4$ may be the same as or different from one another, and are independently selected from among H, $C_1$-$C_6$ alkyl, $C_5$-$C_{10}$ cycloalkyl, $C_6$-$C_{10}$ aryl, and —Si(R$^3$)$_3$ wherein each R$^3$ is independently selected from $C_1$-$C_6$ alkyl.

The synthesis of the above-described germanium precursors can variously be carried out in a ready manner, utilizing synthetic preparations of the types variously shown below. In each instance RMgCl, RMgBr, RMgI, RLi, and RNa can be used as alternative reagents. Further, GeBr$_4$ can be used in place of GeCl$_4$; LiNR$_2$ can be replaced by NaNR$_2$ or KNR$_2$; and Na(C$_5$R$_5$) can be used as an alternative to K(C$_5$R$_5$). Moreover, a multi-step synthetic approach may be employed to generate mixed alkyl species through oxidative addition to a Ge(II) complex to generate Ge(IV) precursors, as shown below:

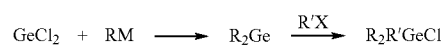

wherein:
R, R', and R'' may be the same as or different from one another, and each is independently selected from H, $C_1$-$C_6$ alkyl, $C_2$-$C_6$ alkenyl, $C_5$-$C_{10}$ cycloalkyl, $C_6$-$C_{10}$ aryl, and —Si(R₃)₃ wherein each $R_3$ is independently selected from $C_1$-$C_6$ alkyl, and M is Li, Na, MgCl, MgBr, or MgI.

Germanium (IV) Precursors for GST Films

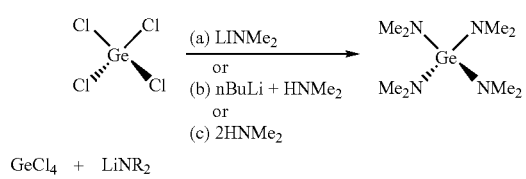

GeCl₄ + LiNR₂

↓

Ge(NR₂)₄

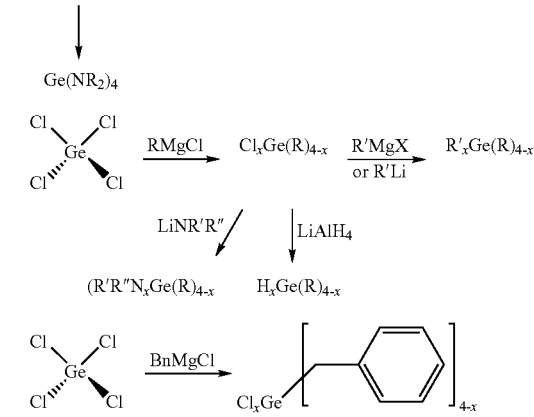

and correspondingly a tetraallylgermanium complex

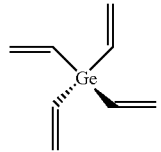

can be formed from such tetrachlorogermanium starting material using a corresponding allyl Grignard reagent R*MgCl, wherein R* is allyl

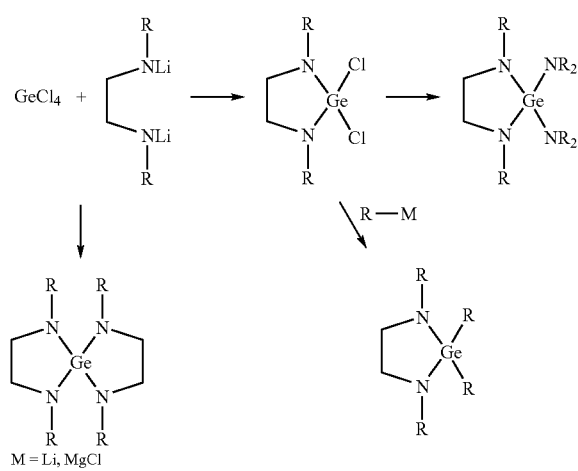

Ge Precursors for GST Films

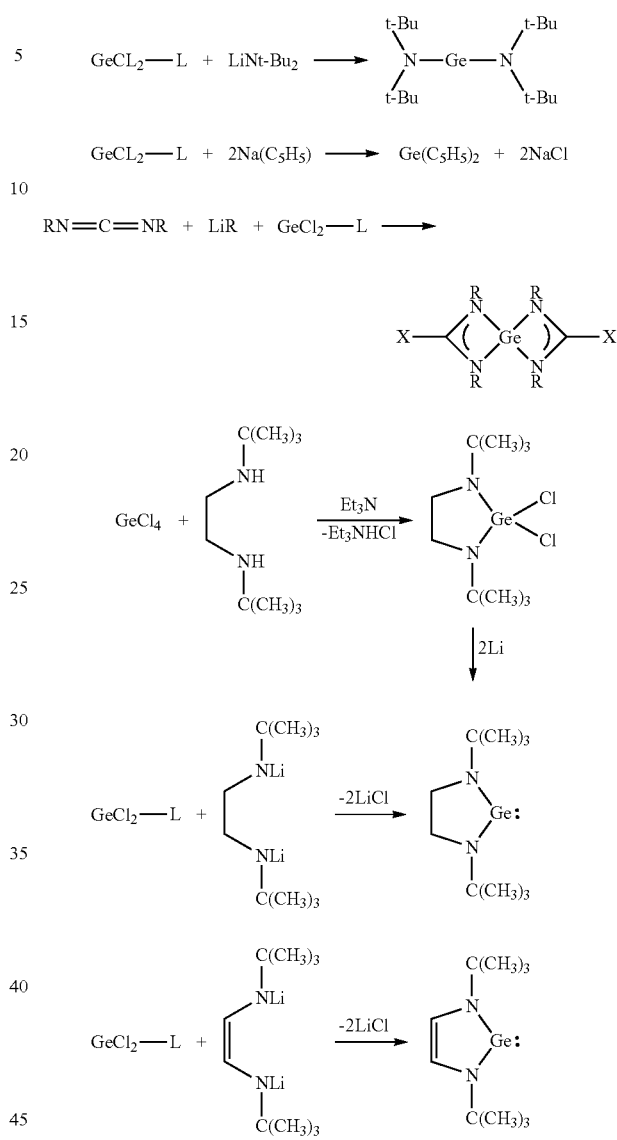

Illustrative Ge(II) compounds that may be usefully employed for CVD or ALD of germanium-containing films include the following:

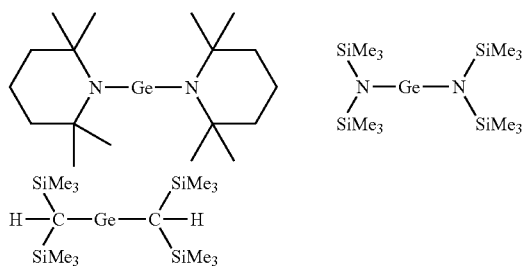

In various embodiments of the invention, dialkylaminoisopropylgermane precursors are used for CVD/ALD formation of GST thin films. Such precursors may be synthesized by a reaction scheme such as that shown below:

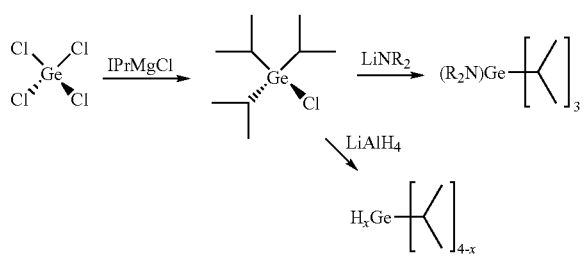

to form germanium complexes such as:

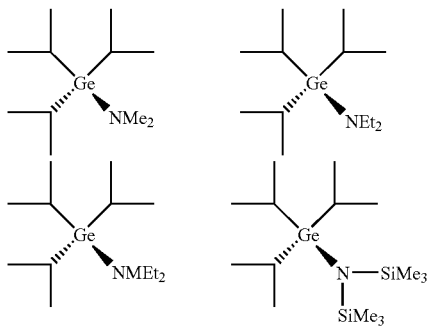

The above-described germanium precursors are useful for CVD and ALD applications, to deposit germanium-containing films on substrates. Tetrakisamidogermanes and triisopropylamines useful for such applications and amenable to transport with a heated bubbler include, for example, Ge(NMe$_2$)$_4$, Ge(NEtMe)$_4$, Ge(NEt$_2$)$_4$, iPr$_3$GeCl, iPr$_3$GeNMe$_2$, iPr$_3$GeNEtMe, and iPr$_3$GeNEt$_2$. The volatility of the germanium precursors of the invention can be readily measured by STA thermogravimetric technique (e.g., by determining material transport under atmospheric pressure in argon) and GC analysis.

In specific embodiments of germanium precursors of the present invention containing alkyl substituents, isopropyl substituents are in many cases preferred over methyl groups due to the ability of the isopropyl substituents to undergo beta-hydrogen elimination, thereby facilitating low temperature decomposition processing of the germanium precursor, without producing significant carbon residue.

Nitrogen containing germanium precursors of the invention have the intrinsic benefit in many applications of mediating some incorporation of nitrogen in final films. In this respect, Si- and N-doped GST materials have lower reset currents, thereby enabling a lower temperature phase-change to occur.

As an additional advantage, various germane precursors of the invention undergo hydrogermolysis coupling reactions to form Ge—Ge bonds, via the reaction R$_3$GeNR'$_2$+R$_3$GeH→R$_3$Ge—GeR$_3$, to yield digermane CVD precursors enabling highly efficient Ge-containing film deposition to be achieved, in relation to mono-germane precursors.

The germanium precursors of the invention can contain a wide variety of ligand species as moieties thereof. Such ligands may for example include, without limitation, allyl, benzyl, t-butyl, cylopentadienyl, hydride, phenyl, and alkyl. Bidentate amines (e.g. N,N-dialkylethylenediamine) can also be used.

The germanium precursors can be delivered in solution or suspension in a liquid delivery technique, using suitable solvent media, or may be delivered for vapor phase desposition of Ge-containing films by solid delivery techniques, e.g., as described hereinabove in respect of the antimony precursors of the invention.

In use as CVD/ALD precursors, the Ge precursor may be deposited separately or in combination with other precursors, e.g., with Sb and Te complexes such as iPr$_3$Sb, Sb(NR$_2$)$_3$, iPr$_2$Te and Te(NR$_2$)$_2$ to form GST films.

One illustrative germanium precursor of the invention is Ge(triisopropyl)(methylethylamide), referred to sometimes hereinafter as GePNEM. This precursor can be employed to deposit germanium on a substrate at suitable deposition process conditions, e.g., deposition temperature in a range of from 300° C. to 450° C., and at pressure ranging from subatmospheric to superatmospheric (e.g., in a range of from about 0.5 torr to 15 atmospheres or more). Set out in Table I below is a listing of film deposition rate, in Angstroms/minute, at varying temperature and pressure conditions, for deposition of germanium on substrates from the GePNEM precursor, delivered to the substrate in a carrier gas flow of hydrogen gas at 200 standard cubic centimeters per minute.

TABLE I

Film Deposition Rate of Germanium Deposited at Varying Temperature and Pressure Conditions

| Temperature (° C.) | Temperature 1/T (K) | Pressure 0.8 torr | Pressure 8 torr |
|---|---|---|---|
| 300 | 0.001745201 | 0.14 Å/min | 0.35 Å/min |
| 320 | 0.001686341 | 0.45 Å/min | |
| 340 | 0.001631321 | 1.32 Å/min | 0.8 Å/min |
| 360 | 0.001579779 | 1.48 Å/min | 1.28 Å/min |
| 380 | 0.001531394 | 2.4 Å/min | 2.7 Å/min |
| 400 | 0.001485884 | 3.4 Å/min | 2.3 Å/min |
| 420 | 0.001443001 | 6.8 Å/min | 10.5 Å/min |
| 440 | 0.001403 | 6.5 Å/min | |

GePNEM Deposition with 200 SCCM H$_2$

In another determination of film thicknesses of germanium achieved by deposition from the GePNEM precursor, deposition carried out for a period of 16 minutes gave the following results: (i) temperature=400° C., pressure=800 millitorr, reactant gas H$_2$, film thickness=57 Å; (ii) temperature=400° C., pressure=800 millitorr, reactant gas NH$_3$, film thickness=94 Å; and (iii) temperature=400° C., pressure=8000 millitorr, reactant gas H$_2$, film thickness=36 Å. These results evidence the suitability of GePNEM for forming germanium or germanium-containing thin films on substrates by vapor deposition techniques.

In various specific embodiments, the invention contemplates a precursor mixture including germanium precursor, antimony precursor and tellurium precursor, wherein at least one of the germanium precursor and antimony precursor includes a precursor selected from among the metal complexes of formulae (A), (B), (C), (D) and (E)(I)-(XVI) described hereinabove.

In another aspect, the invention contemplates additional classes of antimony precursors. Such antimony precursors are suitable for use in forming GST films, in conjunction with the use of suitable germanium and tellurium precursors.

Such additional classes of antimony precursors include those of formulae (F), (G), (H), (I), (J), (K), (L) and (M), as defined below:

(F) aminidates, guanidates and isoureates of the formula:

R$^7{}_n$Sb[R$^1$NC(X)NR$^2$]$_{3-n}$ wherein:
where each $R^1$ and $R^2$ is independently selected from among H, $C_1$-$C_6$ alkyl, $C_5$-$C_{10}$ cycloalkyl, $C_6$-$C_{10}$ aryl, and —Si$(R^3)_3$ wherein each $R^3$ is independently selected from $C_1$-$C_6$ alkyl;
each X is independently selected from among $C_1$-$C_6$ alkoxy, —NR$^4$R$^5$, and —C$(R^6)_3$, wherein
each of $R^4$, $R^5$ and $R^6$ is independently selected from H, $C_1$-$C_6$ alkyl, $C_5$-$C_{10}$ cycloalkyl, $C_6$-$C_{10}$ aryl, and —Si$(R^3)_3$ wherein each $R^3$ is independently selected from $C_1$-$C_6$ alkyl;
each $R^7$ is independently selected from among $C_1$-$C_6$ alkoxy, —NR$^8$R$^9$, and —C$(R^{10})_3$, wherein
each of $R^8$, $R^9$ and $R^{10}$ is independently selected from H, $C_1$-$C_6$ alkyl, $C_5$-$C_{10}$ cycloalkyl, $C_6$-$C_{10}$ aryl, —Si$(R^3)_3$, and —Ge$(R^3)_3$ wherein each $R^3$ is independently selected from $C_1$-$C_6$ alkyl; and
n is an integer from 0 to 3;
(G) tetra-alkyl guanidates of the formula:

wherein:
each of $R^1$ and $R^2$ is independently selected from among H, $C_1$-$C_6$ alkyl, $C_5$-$C_{10}$ cycloalkyl, $C_6$-$C_{10}$ aryl, and —Si$(R^9)_3$ wherein each $R^9$ is independently selected from $C_1$-$C_6$ alkyl;
each of $R^3$ and $R^4$ is independently selected from H, $C_1$-$C_6$ alkyl, $C_5$-$C_{10}$ cycloalkyl, $C_6$-$C_{10}$ aryl, and —Si$(R^9)_3$ wherein each $R^9$ is independently selected from $C_1$-$C_6$ alkyl;
each $R^5$ is independently selected from among $C_1$-$C_6$ alkoxy, —NR$^6$R$^7$, and —C$(R^8)_3$, wherein each of $R^6$, $R^7$ and $R^8$ is independently selected from H, $C_1$-$C_6$ alkyl, $C_5$-$C_{10}$ cycloalkyl, $C_6$-$C_{10}$ aryl, —Si$(R^9)_3$, and —Ge$(R^9)_3$ wherein each $R^9$ is independently selected from $C_1$-$C_6$ alkyl; and
n is an integer from 0 to 3.
(H) carbamates and thiocarbamates of the formula:

wherein:
each X is independently selected from among $C_1$-$C_6$ alkoxy, —NR$^1$R$^2$, and —C$(R^3)_3$, wherein each of $R^1$, $R^2$ and $R^3$ is independently selected from H, $C_1$-$C_6$ alkyl, $C_5$-$C_{10}$ cycloalkyl, $C_6$-$C_{10}$ aryl, and —Si$(R^5)_3$ wherein each $R^5$ is independently selected from $C_1$-$C_6$ alkyl;
each $R^4$ is independently selected from among $C_1$-$C_6$ alkoxy, —NR$^1$R$^2$, and —C$(R^3)_3$, wherein each of $R^1$, $R^2$ and $R^3$ is independently selected from H, $C_1$-$C_6$ alkyl, $C_5$-$C_{10}$ cycloalkyl, $C_6$-$C_{10}$ aryl, and —Si$(R^5)_3$, —Ge$(R^5)_3$ wherein each $R^5$ is independently selected from $C_1$-$C_6$ alkyl;
E is either O or S; and
n is an integer from 0 to 3;
(I) beta-diketonates, diketoiminates, and diketiiminates, of the formulae:

where each of $R^1$, $R^2$, $R^3$ and $R^4$ is independently selected from among H, $C_1$-$C_6$ alkyl, $C_5$-$C_{10}$ cycloalkyl, $C_6$-$C_{10}$ aryl, and —Si$(R^6)_3$ wherein each $R^6$ is independently selected from $C_1$-$C_6$ alkyl;
each X is independently selected from among $C_1$-$C_6$ alkoxy, —NR$^6$R$^7$, and —C$(R^8)_3$, wherein each of $R^6$, $R^7$ and $R^8$ is independently selected from H, $C_1$-$C_6$ alkyl, $C_5$-$C_{10}$ cycloalkyl, $C_6$-$C_{10}$ aryl, and —Si$(R^6)_3$ wherein each $R^6$ is independently selected from $C_1$-$C_6$ alkyl;
each $R^5$ is independently selected from among guanidinate, aminidate, isoureate, allyl, $C_1$-$C_6$ alkoxy, —NR$^9$R$^{10}$, and —C$(R^{11})_3$, wherein each of $R^9$, $R^{10}$ and $R^{11}$ is independently selected from H, $C_1$-$C_6$ alkyl, $C_5$-$C_{10}$ cycloalkyl, $C_6$-$C_{10}$ aryl, —Si$(R^6)_3$, and —Ge$(R^6)_3$ wherein each $R^6$ is independently selected from $C_1$-$C_6$ alkyl; and
n is an integer from 0 to 3.
(J) allyls of the formulae:

 (i)

 (ii)

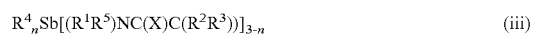 (iii)

 (iv)

where each $R^1$, $R^2$, $R^3$ and $R^5$ is independently selected from among H, $C_1$-$C_6$ alkyl, $C_5$-$C_{10}$ cycloalkyl, $C_6$-$C_{10}$ aryl, and —Si$(R^6)_3$ wherein each $R^6$ is independently selected from $C_1$-$C_6$ alkyl;
each X is independently selected from among $C_1$-$C_6$ alkoxy, —NR$^1$R$^2$, and —C$(R^3)_3$, wherein each of $R^1$, $R^2$ and $R^3$ is independently selected from H, $C_1$-$C_6$ alkyl, $C_5$-$C_{10}$ cycloalkyl, $C_6$-$C_{10}$ aryl, and —Si$(R^6)_3$ wherein each $R^6$ is independently selected from $C_1$-$C_6$ alkyl;
each $R^4$ is independently selected from among guanidinates, aminidates, isoureates, beta-diketonates, diketoiminates, diketiiminates, $C_1$-$C_6$ alkoxy, —NR$^7$R$^8$, and —C$(R^9)_3$, wherein each of $R^7$, $R^8$ and $R^9$ is independently selected from H, $C_1$-$C_6$ alkyl, $C_5$-$C_{10}$ cycloalkyl, $C_6$-$C_{10}$ aryl, —Si$(R^6)_3$, and —Ge$(R^6)_3$ wherein each $R^6$ is independently selected from $C_1$-$C_6$ alkyl; and
n is an integer from 0 to 3.
(L) cyclopentadienyl (Cp) antimony compounds wherein the Cp moiety is of the formulae:

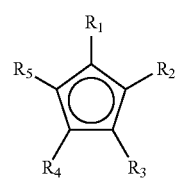

wherein each of $R_1$, $R_2$, $R_3$, $R_4$ and $R_5$ can be the same as or different from the others, and each is independently selected from among hydrogen, $C_1$-$C_{12}$ alkyl, $C_1$-$C_{12}$ alkylamino, $C_6$-$C_{10}$ aryl, $C_1$-$C_{12}$ alkoxy, $C_3$-$C_6$ alkylsilyl, $C_2$-$C_{12}$ alkenyl, $R^1R^2NNR^3$, wherein $R^1$, $R^2$ and $R^3$ may be the same as or different from one another and each is independently selected from $C_1$-$C_6$ alkyl, and pendant ligands including functional group(s) providing further coordination to the antimony central atom, and selected from among aminoalkyl, alkoxyalkyl, aryloxyalkyl, imidoalkyl, and acetylalkyl, having the following formulae:

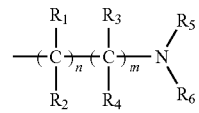

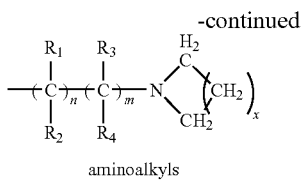

aminoalkyls wherein: the methylene (—CH$_2$—) moiety could alternatively be another divalent hydrocarbyl moiety; each of R$_1$-R$_4$ is the same as or different from one another, with each being independently selected from among hydrogen, C$_1$-C$_6$ alkyl and C$_6$-C$_{10}$ aryl; each of R$_5$ and R$_6$ is the same as or different from the other, with each being independently selected from among C$_1$-C$_6$ alkyl; n and m are each selected independently as having a value of from 0 to 4, with the proviso that m and s n cannot be 0 at the same time, and x is selected from 1 to 5;

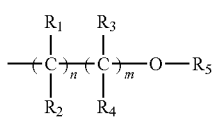

alkoxyalkyls and aryloxyalkyls wherein each of R$_1$-R$_4$ is the same as or different from one another, with each being independently selected from among hydrogen, C$_1$-C$_6$ alkyl, and C$_6$-C$_{10}$ aryl; R$_5$ is selected from among C$_1$-C$_6$ alkyl, and C$_6$-C$_{10}$ aryl; and n and m are selected independently as having a value of from 0 to 4, with the proviso that m and n cannot be 0 at the same time;

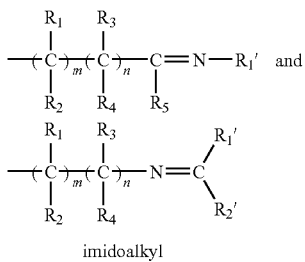

imidoalkyl wherein each of R$_1$, R$_2$, R$_3$, R$_4$, R$_5$ is the same as or different from one another, with each being independently selected from among hydrogen, C$_1$-C$_6$ alkyl, and C$_6$-C$_{10}$ aryl; each of R$_1'$, R$_2'$ is the same as or different from one another, with each being independently selected from C$_1$-C$_6$ alkyl, and C$_6$-C$_{10}$ aryl; and n and m are selected independently from 0 to 4, with the proviso that m and n cannot be 0 at the same time;

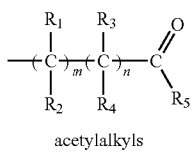

acetylalkyls wherein each of R$_1$-R$_4$ is the same as or different from one another, with each being independently selected from among hydrogen, C$_1$-C$_6$ alkyl, and C$_6$-C$_{10}$ aryl; R$_5$ is selected from among C$_1$-C$_6$ alkyl, C$_6$-C$_{10}$ aryl, and C$_1$-C$_5$ alkoxy; and n and m are selected independently from 0 to 4, with the proviso that m and n cannot be 0 at the same time;

wherein non-Cp ligand(s) of the antimony Cp compound can optionally include ligands selected from the group consisting of guanidinates, aminidates, isoureates, allyls, beta-diketonates, diketoiminates, and diketiiminates; and (M) alkyls, alkoxides and silyls with pendent ligands, of the formulae:

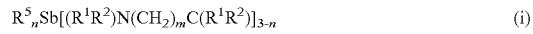

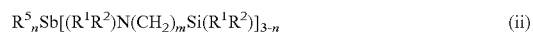

where each of R$^1$ and R$^2$ is independently selected from among H, C$_1$-C$_6$ alkyl, C$_5$-C$_{10}$ cycloalkyl, C$_6$-C$_{10}$ aryl, and —Si(R$^3$)$_3$ wherein each R$^3$ is independently selected from C$_1$-C$_6$ alkyl;

each R$^5$ is independently selected from among guanidinates, aminidates, isoureates, beta-diketonates, diketoiminates, diketiiminates, C$_1$-C$_6$ alkoxy, —NR$^6$R$^7$, and —C(R$^8$)$_3$, wherein each of R$^6$, R$^7$ and R$^8$ is independently selected from H, C$_1$-C$_6$ alkyl, C$_5$-C$_{10}$ cycloalkyl, C$_6$-C$_{10}$ aryl, —Si(R$^3$)$_3$, and —Ge(R$^3$)$_3$ wherein each R$^3$ is independently selected from C$_1$-C$_6$ alkyl;

n is an integer from 0 to 3;

m is integer from 0 to 4.

Antimony precursors of a general type within the foregoing classes (F)-(M) include precursors having the following structures, wherein the various "R" groups in these structures are not necessarily numbered in exact correspondence with the substituent numberings in the above formulae, but nonetheless reflect the substituted positions in general fashion, which will be understood in reference to the above definitions of the substituents at the various positions of the associated molecules.

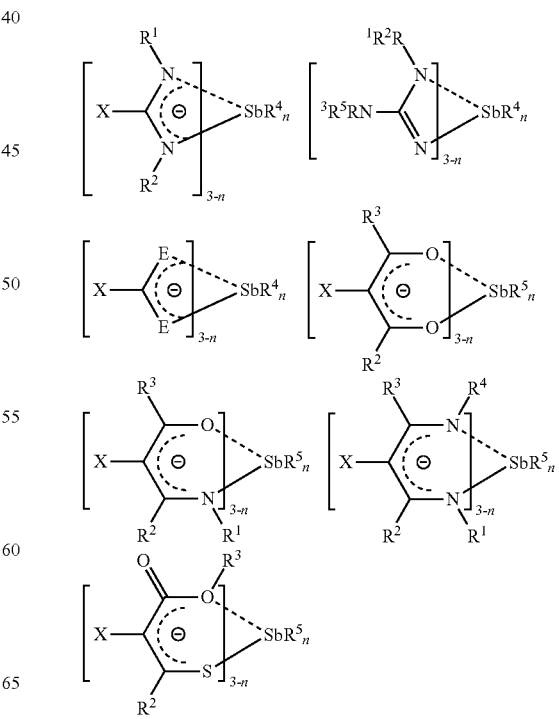

-continued

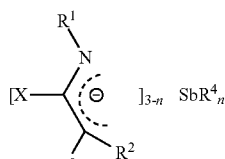

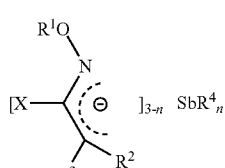

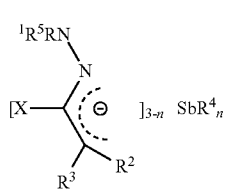

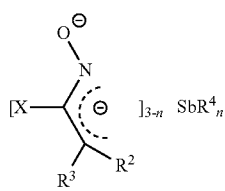

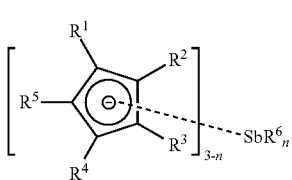

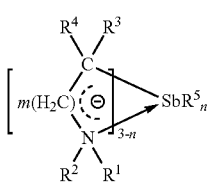

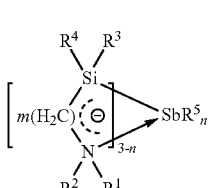

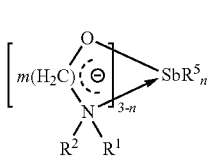

including the following illustrative complexes:

A

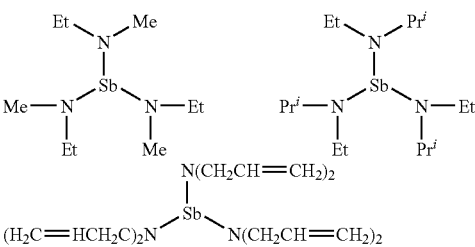

B antimony amides of the formulae

C antimony (III) alkyl/amino precursors of the formulae:

D and stibenes with germanium anions, of the formulae:

A

B

C

The antimony precursors of classes (F)-(M) are usefully employed for deposition of antimony at low temperature with reducing co-reactants, e.g., reactants such as hydrogen, $H_2$/plasma, amines, imines, hydrazines, silanes, silyl chalcogenides such as (Me$_3$Si)$_2$Te, germanes such as GeH$_4$, ammonia, alkanes, alkenes, and alkynes.

The antimony precursors may be delivered for such deposition via liquid delivery techniques, in which precursors that are liquids may be used in neat liquid form, and precursors that are solids or liquids may be delivered in solutions or suspensions, in combination with suitable solvents, such as alkane solvents (e.g., hexane, heptane, octane, and pentane), aryl solvents (e.g., benzene or toluene), amines (e.g., triethylamine, tert-butylamine), imines and hydrazines. The utility of specific solvent compositions for particular antimony precursors can be readily empirically determined, to select an appropriate single component or multicomponent solvent medium for liquid delivery vaporization and transport of the specific antimony precursor that is employed.

In another aspect of the invention, solid delivery techniques may be employed, in which the solid precursor is volatilized, to form a precursor vapor that is delivered to the deposition chamber for forming an antimony or antimony-containing film on the substrate. The solid precursor may be packaged for such use in a storage and dispensing package of suitable character, such as the ProE-Vap solid delivery and vaporizer unit commercially available from ATMI, Inc. (Danbury, Conn., USA).

The invention also contemplates the use of antimony, germanium and tellurium precursors of the present invention separately for deposition of antimony-containing films, germanium-containing films, and tellurium-containing films, respectively. Thus, an antimony precursor of the invention may be employed to deposit an antimony-containing film. In another embodiment, a germanium precursor of the invention may be employed to form a germanium-containing film. In another embodiment, a tellurium precursor of the invention may be employed to form a tellurium-containing film. In still another embodiment, an antimony precursor of the invention and a germanium precursor of the invention may be utilized to form an antimony/germanium film. In yet another embodiment, an antimony precursor of the invention can be utilized in combination with a tellurium precursor, to form an antimony/tellurium film. Another embodiment of the invention involves use of a germanium precursor of the invention in combination with a tellurium precursor, to form a germanium/tellurium film.

The antimony and/or germanium precursors of the invention can be used to deposit Ge$_2$Sb$_2$Te$_5$ films on suitable microelectronic device substrates in the fabrication of phase change memory devices.

Such GST films can be fabricated using continuous CVD or ALD techniques using suitable germanium, antimony and tellurium precursors, with at least one of the germanium and antimony precursors comprising a metal complex of the present invention. The precursors may be supplied in appropriate ratios to yield the GST film of desired character. For example, ALD may be performed with the precursors (Ge, Sb, Te) being pulsed in a manner to control composition of the resulting film, e.g., with a pulse cycle including a sequential introduction of precursor species in the sequence Te—Ge—Te—Sb—Te—Ge—Te—Sb—Te, repetitively conducted until a desired film thickness has been achieved.

As another variant of deposition techniques that may advantageously be employed to form films containing antimony and/or germanium, by use of precursors of the present invention, other co-reactant species may be added in the deposition operation, to compositionally modify the resulting film. Examples include use of co-reactants to compositionally modify the film for oxygen and/or nitrogen incorporation, e.g., with very small amounts of N$_2$O, O$_2$ and NO.

In other embodiments, atomic layer deposition (ALD) and rapid vapor deposition (RVD) techniques may be employed to deposit films containing antimony and/or germanium using precursors of the present invention. For example, a rapid surface catalyzed vapor deposition may be employed using ALD, in which a first precursor vapor is contacted with the substrate to form a saturated surface layer of the precursor, followed by exposure to a second precursor vapor, and thereafter by exposure to a third precursor vapor, with inert gas purges being carried out between the respective precursor vapor contacting steps, in which at least one of the first, second and third precursors comprises an antimony and/or germanium precursor of the invention and, and in which the precursor contacting and intervening purge steps are repetitively conducted until a predetermined thickness of deposited film material has been achieved.

More generally, the present invention contemplates a wide variety of antimony and germanium complexes that can be utilized to form corresponding Sb- and Ge-containing films. The precursor complexes and compositions of the invention accordingly can be varied in specific usage, and can comprise, consist, or consist essentially of specific metal source reagents, or such specific reagents and other precursor species. Further, it may be desirable in some applications to employ multiple precursor species of the invention, in combination with one another and/or together with other precursor species.

The invention also contemplates specific structural definitions and/or specifications of precursor complexes in specific embodiments, and the exclusion of specific moieties, ligands and elemental species in specific embodiments. As an illustrative example, in homoleptic tris(dialkylamido)antimony complexes and tetrakis(dialkylamido)germanium complexes of the invention, the alkyl substituents may exclude methyl. As another example, tetrakisdialkylamidogermanes may be excluded in certain embodiments of the invention. As a still further example, in germanyl and silyl antimony complexes of the invention, trimethylgermanyl and trimethylsilyl species may for example be excluded. It will therefore be appreciated that the invention admits of delimited complexes and compositional features of complexes in various particularized embodiments of the invention, for purposes of identifying precursor complexes and classes of same that are preferred implementations of the invention in certain applications thereof.

The synthesis of ethylmethylaminotriisopropylgermane is now described to show the details of making an illustrative germanium precursor of the invention.

Example 1

Synthesis of Ethylmethylaminotriisopropylgermane

A solution of nBuLi (2M in hexanes, 26.34 mL, 42.14 mmol) was slowly added to an ice-cooled solution of ethylmethylamine (3.98 mL, 46.35 mmol) in ether (100 mL). The resulting white mixture was stirred for 2 hours. Triisopropylchlorogermane (9.16 mL, 42.14 mmol) was added dropwise and the reaction mixture slowly warmed to room temperature. The mixture was stirred overnight, the solvent evaporated under vacuum, and the residue washed with pentane (100 mL). The mixture was filtered through a medium glass frit under nitrogen and the solvent evaporated under vacuum to give 10.7 g, 98% of a colorless liquid. The product was purified by fractional distillation (40° C., 75 mtorr). $^1$H NMR (C$_6$D$_6$): δ 2.87 (q, 2H, $^3$J=6.9 Hz, NCH$_2$CH$_3$), 2.62 (s, 3H, NCH$_3$), 1.36 (m, CH(CH$_3$)$_2$), 1.18 (d, 18H, $^3$J=7.2 Hz, CH(CH$_3$)$_2$), 1.11 (t, 3H, $^3$J=6.9 Hz, NCH$_2$CH$_3$). $^{13}$C NMR (C$_6$D$_6$): δ 48.42, 38.22 (NCH$_2$CH$_3$, NCH$_3$), 20.19 (CH (CH$_3$)$_2$), 16.20, 15.79 (NCH$_2$CH$_3$, CH(CH$_3$)$_2$).

Figure 4D:
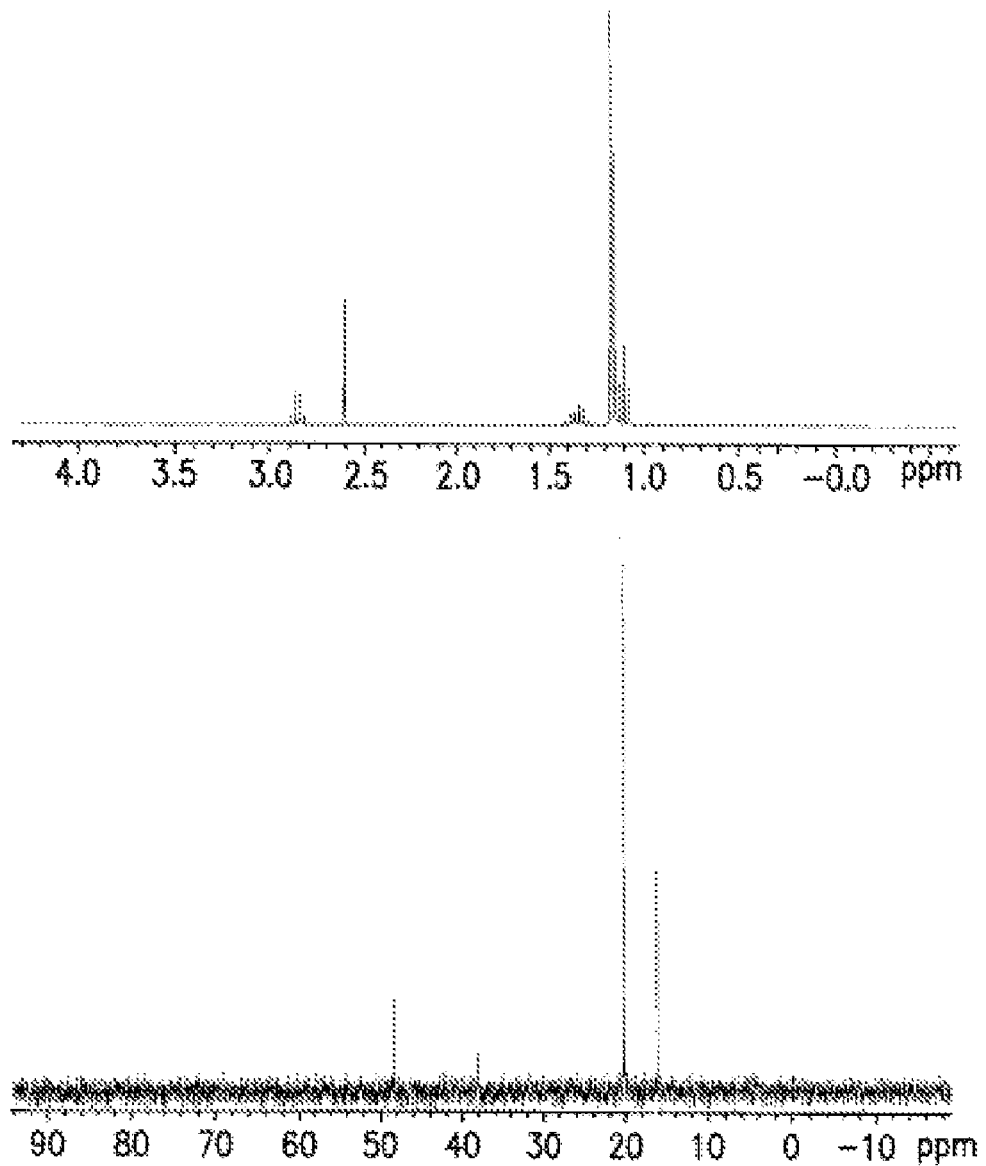
FIG. 4(d) shows the nuclear magnetic resonance spectrum of iPr$_3$GeNEtMe.

FIG. 4(a) is a gas chromatography (GC) spectrum for such ethylmethylaminotriisopropylgermane product, and FIG. 4(b) is a corresponding tabulation of peak data for such GC spectrum. FIG. 4(c) is a mass spectrum for the ethylmethylaminotriisopropylgermane product. FIG. 4(d) shows the nuclear magnetic resonance spectrum of the ethylmethylaminotriisopropylgermane product.

Figure 5:
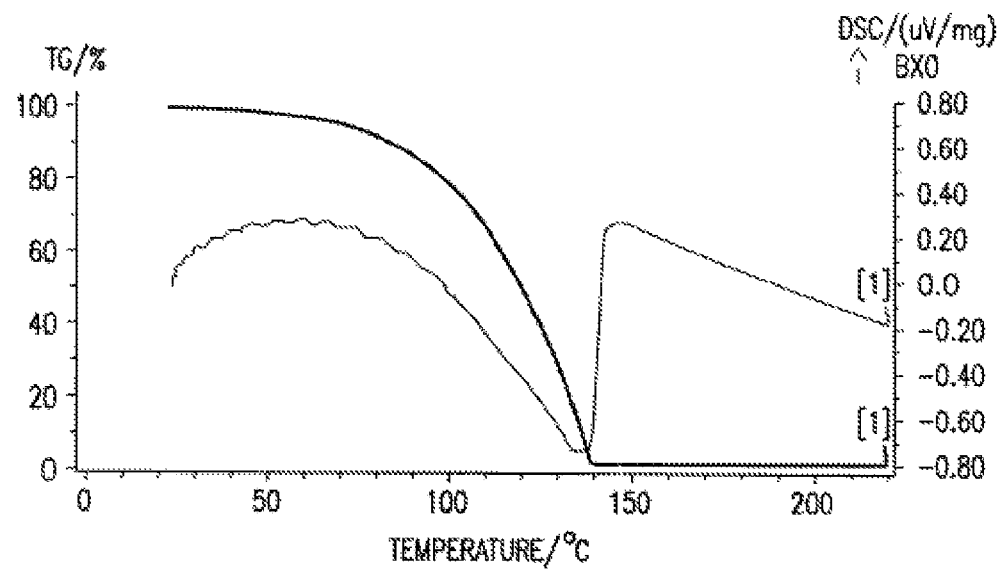
FIG. 5 is an STA spectrum of the ethylmethylaminotriisopropylgermane product, showing differential scanning calorimetry (DSC) data and thermogravimetric (TG) data, as a function of temperature.

FIG. 5 is an STA spectrum of the ethylmethylaminotriisopropylgermane product, showing differential scanning calorimetry (DSC) data and thermogravimetric (TG) data, as a function of temperature.

Another aspect of the invention relates to tellurium complexes with beta-diketiminate ligands, which overcome the problems that many tellurium precursors used in deposition applications are very oxygen-sensitive and light-sensitive, and have an unpleasant odor. By base stabilization with beta-diketiminate ligands, a tellurium precursor is obtained of a highly stable character with improved handling and shelf life characteristics, reduced odor, and sufficient volatility for deposition applications.

The tellurium diketiminate complexes of the invention can be used for CVD/ALD to form Te or Te-containing films. These compounds can be used in combination with Ge- and/or Sb-compounds to produce Te—Ge—, Te—Sb— or Ge—Sb—Te films in varied compositions. A general procedure to synthesize diketiminate ligands has been described in the literature, but such procedure is disadvantageous, since very bulky aryl substituents on the coordinating nitrogen atoms are required.

In contrast, we have discovered that smaller alkyl ligands as iso-propyl, n-butyl, tert-butyl or amine-substituted alkyl groups, as for example ethylene-dimethylamine, can be advantageously used to produce superior tellurium diketiminate precursors for CVD/ALD applications. Smaller substituents on the nitrogen donor atoms provide sufficient volatility to form good films at low temperature.

The ligands L can be used as the lithium salt or in a free imine form to synthesize the desired Te complexes. The lithium salt of the ligand can be reacted with TeX$_4$ (wherein X=Cl, Br, I) to generate LTeX$_3$ by salt elimination, which can then be reacted with either a lithium or a Grignard reagent to produce LTeR$_3$ (wherein R=alkyl, aryl, amide, silyl).

Alternatively the free imine form of the ligand L can be reacted with a tellurium organic compound such as TeMe$_4$ to produce the desired Te species LTeMe$_3$ by methane elimination. The diketiminate ligands provide very effective base stabilization of the reactive metal center tellurium. The invention therefore provides a new class of Te complexes that provide greater stability and shelf life, while retaining sufficient volatility to form superior Te films via CVD/ALD at low temperatures.

The tellurium complexes of the invention have the formulae (I) and (II):

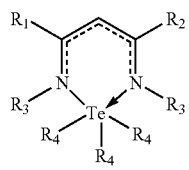

(I)

wherein R$_1$, R$_2$ and R$_3$ they be the same as or different from one another, and each is independently selected from C$_1$-C$_6$ alkyl, C$_6$-C$_{10}$ aryl, silyl and C$_1$-C$_{12}$ alkylamine (which includes both monoalkylamine as well as dialkylamine); and

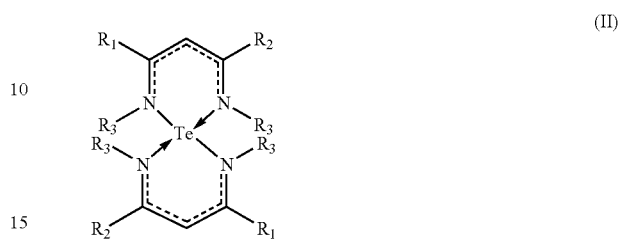

(II)

wherein R$_1$, R$_2$ and R$_3$ they be the same as or different from one another, and each is independently selected from C$_1$-C$_6$ alkyl, C$_6$-C$_{10}$ aryl, silyl and C$_1$-C$_{12}$ alkylamine (which includes both monoalkylamine as well as dialkylamine).

The beta-diketiminate ligands may for example be synthesized by the following procedure:

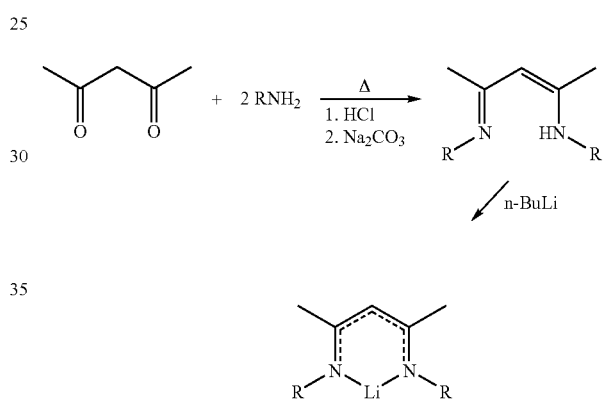

with R = alkyl, aryl, silyl, alkylamine

The tellurium complexes then can be synthesized by the following reaction:

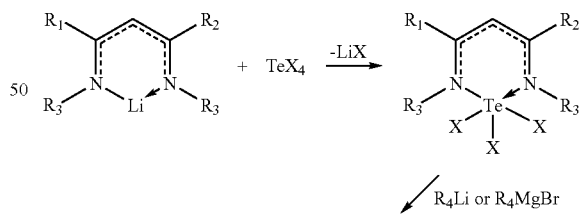

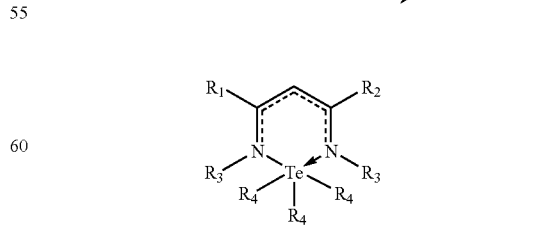

with X = Cl, Br, I

R$_1$, R$_2$, R$_3$, R$_4$ = alkyl, aryl, silyl, alkylamine or alternatively by the following synthesis reaction:

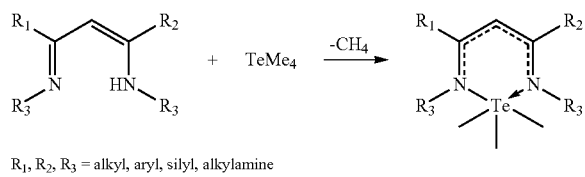

R₁, R₂, R₃ = alkyl, aryl, silyl, alkylamine or by the following synthesis reaction:

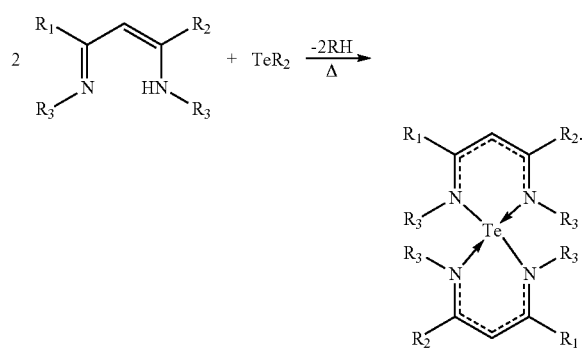

R, R₁, R₂, R₃ = alkyl, aryl, silyl, alkylamine

The tellurium complexes of the invention are usefully employed as CVD/ALD precursors for deposition of tellurium-containing thin films, e.g., by liquid injection of neat precursor material, or in organic solvent or by direct evaporation.

The invention in another aspect relates to germanium complexes and their use in CVD/ALD for forming germanium-containing films, e.g., GST films, wherein the germanium complexes are selected from among:

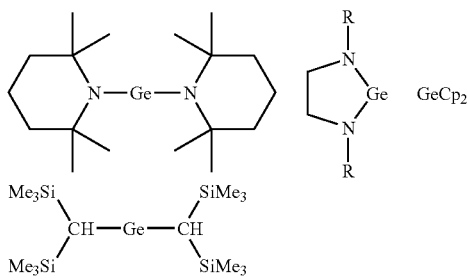

wherein the R groups in the second formula may be the same as or different from one another, and each is independently selected from among H, $C_1$-$C_6$ alkyl, $C_6$-$C_{10}$ aryl, $C_3$-$C_8$ cycloalkyl, heteroatom groups, and other organo groups.

Another aspect of the invention relates to digermane and strained ring germanium precursors for CVD/ALD of germanium-containing thin films. Previously employed germanium precursors such as germane that have been used for forming GST (germanium-antimony-tellurium) films for phase change memory devices require very high temperature deposition conditions. This in turn makes it difficult to form a pure $Ge_2Sb_2Te_5$ phase material. The present invention overcomes this deficiency in the provision of precursors having a high vapor pressure at ambient conditions, which are useful to deposit germanium-containing films at temperatures below 300° C.

Germanium-germanium bonds are inherently weak (~188 kJ/mole) and become less stable with electron withdrawing substituents such as chlorine or $NMe_2$. Such bonds can readily dissociate to form $R_3Ge$ radicals under UV photolysis or thermolysis, or by chemical oxidation using peroxides, ozone, oxygen or plasma. Commercially available digermanes include hydride, methyl, phenyl, or ethyl groups that require high temperatures for decomposition and the resulting films are often contaminated with carbon residues.

We have overcome such deficiency by the provision of germanium complexes using as ligands isopropyl, isobutyl, benzyl, allyl, alkylamino, nitriles, or isonitriles to achieve complexes that enabled the deposition of pure germanium metal films at low temperatures. In addition, the invention contemplates strained-ring germanium complexes (e.g., germacyclobutane) that can undergo thermal ring opening to generate a diradical intermediate that readily dissociates to germylene fragments. The bond dissociation energy of the strained Ge—C bond (63 kcal/mol) is considerable lower than Ge—$CH_3$ (83 kcal/mol), thereby enabling lower temperature film deposition of germanium to be achieved, than has been achievable with the aforementioned conventional germanium precursors.

The germanium complexes of the invention include those of formulae (I)-(III) below:

(I) alkyldigermanes of the formula

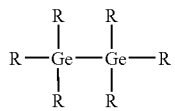

wherein each R may be the same as or different from the others, and each is independently selected from among isopropyl, isobutyl, benzyl, allyl, alkylamino, nitriles, and isonitriles;

(II) alkyl(dialkylamino)germanes of the formula

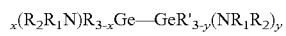

$_x(R_2R_1N)R_{3-x}Ge$—$GeR'_{3-y}(NR_1R_2)_y$ wherein each R may be the same as or different from the others, and each is independently selected from among isopropyl, isobutyl, benzyl, allyl, alkylamino, nitriles, and isonitriles; and (III) strained-ring germane complexes of the formula:

wherein each of $R_1$, $R_2$, $R_3$ and $R_4$ may be the same as or different from the others, and each is independently selected from among H, $C_1$-$C_6$ alkyl, $C_6$-$C_{10}$ aryl, $C_3$-$C_8$ cycloalkyl, or a heteroatom group.

The complexes (I) can be synthesized, by way of example, according to the following synthesis process:

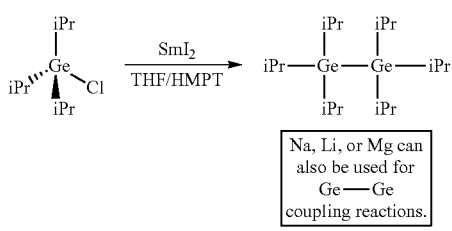

or by the following synthesis:

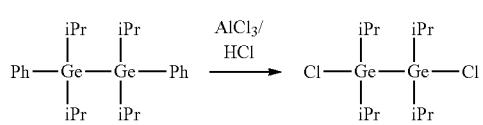

or by a synthesis such as the following:

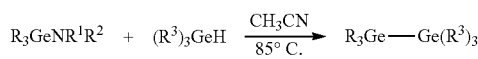

or a synthesis procedure such as:

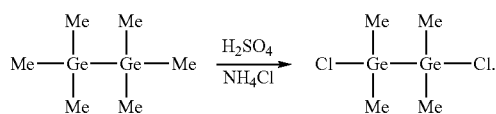

The germanium complexes of formula (II) can be formed by the following illustrated procedure:

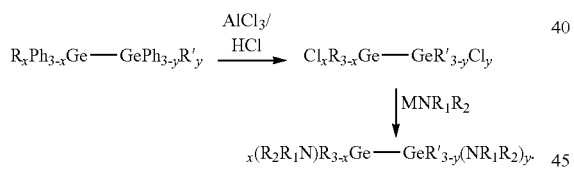

Illustrative synthesis processes that can be employed for forming germanium complexes of formula (III) includes the following:

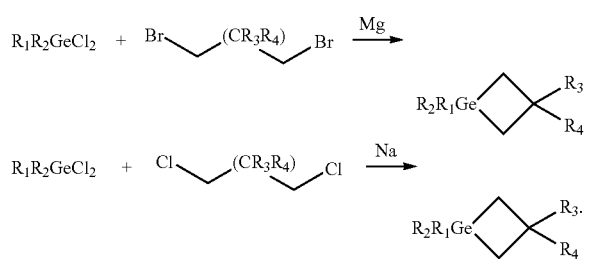

The strained ring alkylgermanes are usefully employed as CVD/ALD precursors for forming germanium-containing thin films on substrates involving reactions such as those illustratively shown below.

Strained Ring Alkylgermanes as CVD/ALD Precursors for Thin Metal Films

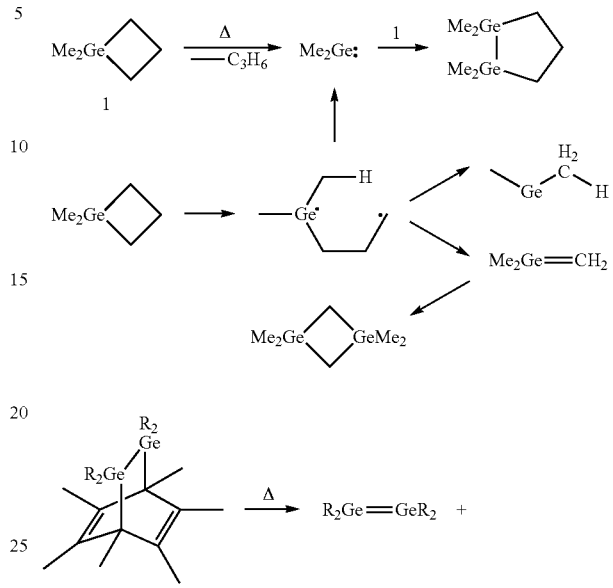

Another aspect of the invention relates to a single-source precursor for germanium and tellurium, as useful in the formation of GST films. Such single-source of germanium telluride precursors may be used in combination with an antimony precursor for GST film formation, optionally with co-reactants as may be desirable to provide films of appropriate stoichiometry for a given application.

The germanium telluride complexes of the invention in one aspect include dialkylgermanetellurones. Suitable dialkylgermanetellurones can be synthesized by oxidative addition reaction of germanium (II) dialkyls with elemental tellurium powder in a solvent medium such as tetrahydrofuran (THF). In some instances so it may be desirable to conduct the reaction in the absence of light, depending on the light-sensitivity of the product germanium-tellurium complex. An illustrative synthesis procedure is set out below:

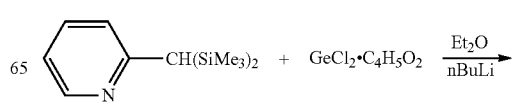

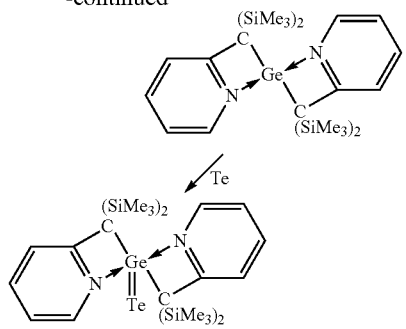

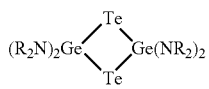

The single-source Ge—Te precursors of the invention can be advantageously used to facilitate lower temperature deposition processes or to increase GST film growth rates in specific applications.

Germanium tellurides of the invention, in another embodiment, can be formed by the following synthesis procedure:

Germanium Telluride ALD/CVD Precursors

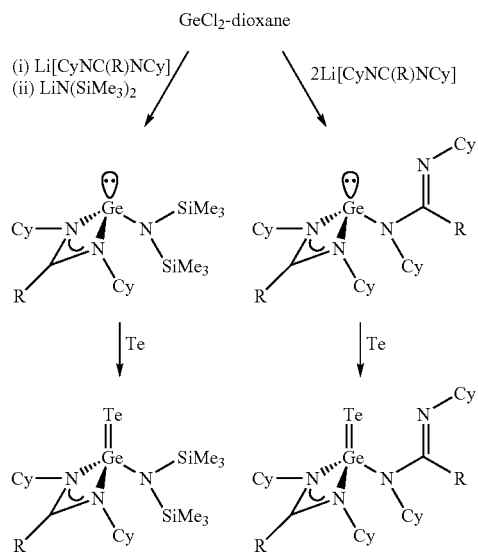

Other germanium telluride complexes can be formed by the following synthesis process:

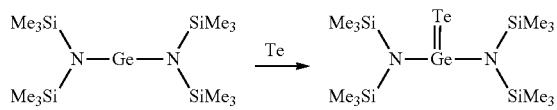

or by the following generalized reactions:

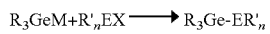

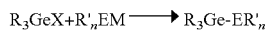

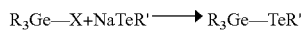

wherein E is tellurium; M is Li, Na, or K, X is chlorine, bromine or iodine; and the R and R' groups may be the same as or different from one another, and each is independently selected from among H, $C_1$-$C_6$ alkyl, $C_6$-$C_{10}$ aryl, $C_3$-$C_8$ cycloalkyl, heteroatom groups, and other organo groups.

One Ge—Te complex of the invention is:

wherein each of the R substituents may be the same as or different from one another, and is independently selected from among H, $C_1$-$C_6$ alkyl, $C_6$-$C_{10}$ aryl, $C_3$-$C_8$ cycloalkyl, heteroatom groups, and other organo groups.

Another aspect of the present invention relates to highly unsymmetric germanium complexes based on amide ligands, which are useful for low temperature (below 300° C.) deposition of a germanium-antimony-tellurium ($Ge_2Sb_2Te_5$) thin film by a CVD or ALD process. These complexes are selected from among complexes of formulae (I) and (II):

Formula (I):

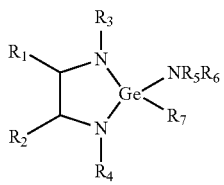

Formula (II):

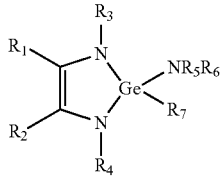

wherein $R_1$, $R_2$, $R_3$, $R_4$, $R_5$, $R_6$ and $R_7$ may be the same as or different from one another, and each is independently selected from the group consisting of $C_1$-$C_6$ alkyl, $C_6$-$C_{10}$ aryl, silyl, alkylsilyl (e.g., trimethylsilyl), hydrogen and halogen, or wherein in lieu of —$NR_5R_6$, the substituent coordinated to the germanium central atom is instead selected from the group consisting of $C_1$-$C_6$ alkyl, $C_3$-$C_8$ cycloalkyl, $C_6$-$C_{10}$ aryl, or halide.

The precursors of formulae (I) and (II) can be delivered to the CVD or ALD chamber by liquid delivery techniques, in which the precursor is dissolved or suspended in a suitable solvent medium. Illustrative of solvent media that may be employed in the broad practice of the present invention are solvents selected from among alkanes (e.g., hexane, heptane, octane and pentane), aromatics (e.g., benzene or toluene), or amines (e.g., triethylamine or tert-butylamine). The precursors can also be delivered as neat liquids, or alternatively by solid delivery techniques, utilizing suitable packaging for volatilization and dispensing. One preferred solid delivery package is the ProE-Vap™ solid delivery and vaporizer unit, commercially available from ATMI, Inc. (Danbury, Conn., USA).

The germanium complexes of formulae (I) and (II) can be synthesized according to the following synthesis schemes, in illustrative embodiments.

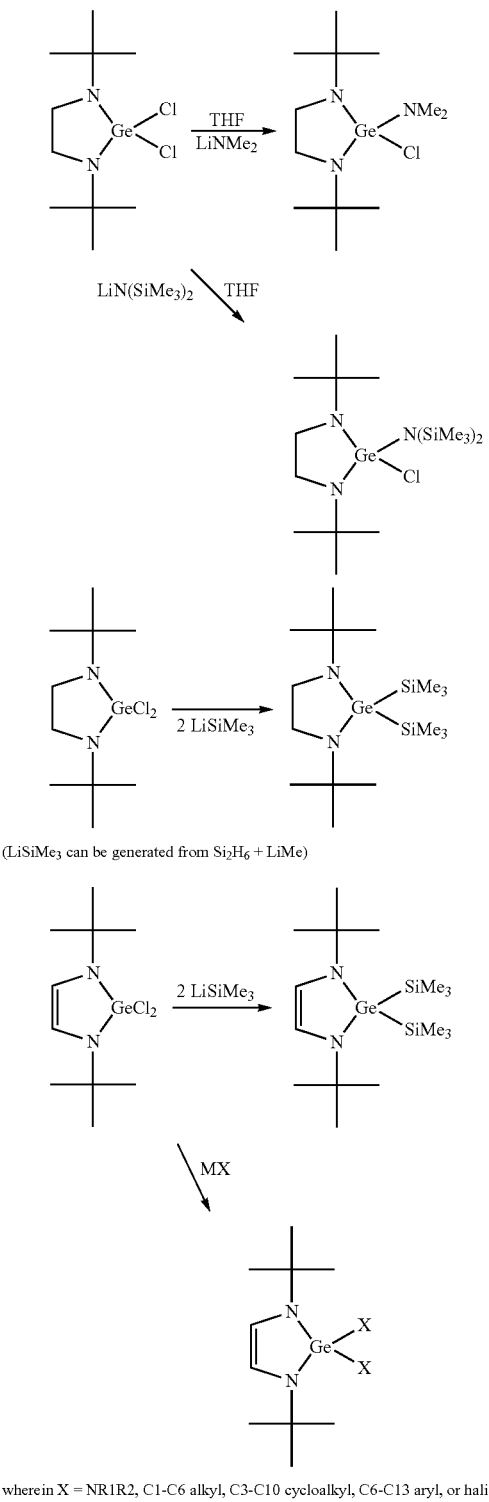

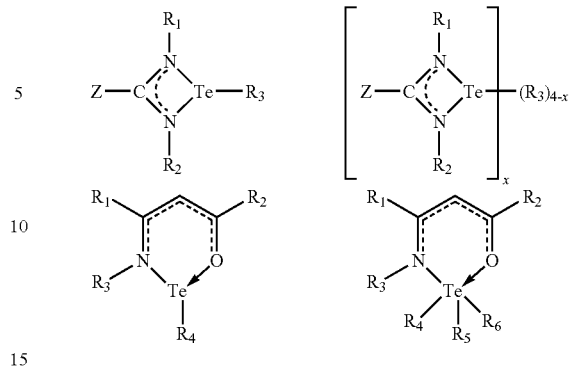

wherein $R_1$, $R_2$, $R_3$, $R_4$, $R_5$, $R_6$ and Z may be the same as or different from one another, and each is independently selected from the group consisting of $C_1$-$C_6$ alkyl, $C_3$-$C_8$ cycloalkyl, $C_6$-$C_{10}$ aryl, silyl, alkylsilyl (e.g., trimethylsilyl), hydrogen and halogen, and wherein x is an integer having a value of from 1 to 3.

In another aspect, the invention relates to germanium precursors useful in phase change memory device fabrication based on chalcogenide materials that undergo a phase change upon heating and are read out as "0" or "1" based on their electrical resistivity, which changes whether the phase change material in the memory cell is in a crystalline or amorphous state. Chalcogenide materials comprise a large number of binary, ternary, and quaternary alloys of a number of metals and metalloids, e.g., GeSbTe, GeSbInTe, and many others.

Phase change memory devices require relatively pure alloys, with well controlled composition. Current processes utilize physical vapor deposition to deposit thin films of these materials. CVD and ALD methods are desirable for their inherent scalability to large area wafers and for composition control. A major deficiency in the current art is the high deposition temperature needed with current alkyl (e.g., $Me_3Sb$, $Me_2Te$) or halide sources, which typically greatly exceed 300° C. and may be as high as 500° C., which exceeds the allowable thermal budget for device integration and can result in the evaporation of the chalcogenide material.

The invention in another aspect relates to various materials and processes that enable low temperature deposition of chalcogenide alloys.

In one chemical approach, butyl and propyl (especially t-butyl and iso-propyl) substituted alkyl hydrides are employed as precursor complexes, e.g., complexes of the formula $iPr_xMH_{y-x}$, wherein: x>1; y=oxidation state of the metal (M) center; and y−x may=0.

In another chemical approach, butyl and propyl (especially t-butyl and iso-propyl) substituted alkyl halides are employed as precursor complexes, e.g., complexes of the formula $iPr_xMX_{y-x}$, wherein: X=F, Cl, Br; x>1; y=oxidation state of the metal (M) center; and y−x may=0.

Such precursors can enhance deposition at lower temperatures via beta hydrogen elimination.

In another embodiment, digermanes are employed to lower the incorporation temperature of germanium. Useful compounds in this respect include $Ge_2H_6$, $Ge_2Me_6$, or $Ge_2Et_6$. $Ge_2iPr_6$ and $Ge_2tBu_6$, as well as $Ge_2(SiMe_3)_6$ and $Ge_2Ph_6$, in which Me=methyl, Et=ethyl, iPr=isopropyl, tBu=t-butyl, and Ph=phenyl.

More generally, compounds of the formula $Ge_2R_6$ may be employed, wherein each of the R's can be the same as or different from the others, and each is independently selected from among H, $C_1$-$C_8$ alkyl, $C_1$-$C_8$ fluoroalkyl, $C_6$-$C_{12}$ aryl, $C_6$-$C_{12}$ fluoroaryl, $C_3$-$C_8$ cyclo-alkyl, $C_3$-$C_8$ cyclo-fluoroalkyl. In addition, $Ge_2R_4$ compounds including $Ge_2Ph_4$ can be usefully employed for such purpose, wherein each of the R groups may be as above defined. Additional complexes may be utilized including 5-member ring complexes with Ge in the ring. Ge(II) complexes are also potentially useful in specific applications, such as cyclopentadienyl compounds of the formula $Ge(CpR_5)_2$ wherein Cp is cyclopentadienyl and each of the R's may be the same as or different from one another and each is independently selected as above. Another germanium compound that is usefully employed for phase change memory applications is $Ge(CH(SiMe_3))_2$.

In another aspect, the antimony component of GST films can be supplied from a precursor such as triphenylantimony, which is inexpensive and light-sensitive in character, and has utility in light/UV-activated deposition processes.

Delivery approaches for precursor delivery to enable low temperature deposition of chalcogenide alloys include the use of separate bubblers for in each precursor for the phase change memory film, liquid injection of precursor mixtures as an approach to manage disparate volatility characteristics of the several precursors to enable delivery of precise volumetric flows at desired compositions, and the use of mixtures of neat liquid or precursor/solvent compositions, as respective techniques that may be useful in specific applications.

Film deposition approaches for low temperature deposition of chalcogenide alloys include: the use of continuous CVD in thermal mode, optionally with reducing gases such as hydrogen; employment of pulsed or atomic layer deposition to separate the dose step from the co-reactant such as hydrogen plasma; employment of activation techniques such as UV or other light sources that are "tuned" to the precursor, with a light being continuous with the precursor dosing, or dosed separately to avoid gas-phase reactions; and use of alternative reductive co-reactants such as germane ($GeH_4$) advantageously dispensed from sub-atmospheric delivery systems, such as the SAGE® dispensing package commercially available from ATMI, Inc. (Danbury, Conn., USA), for enhanced safety and reduced cost of ownership for the source gas for the deposition.

Figure 6:
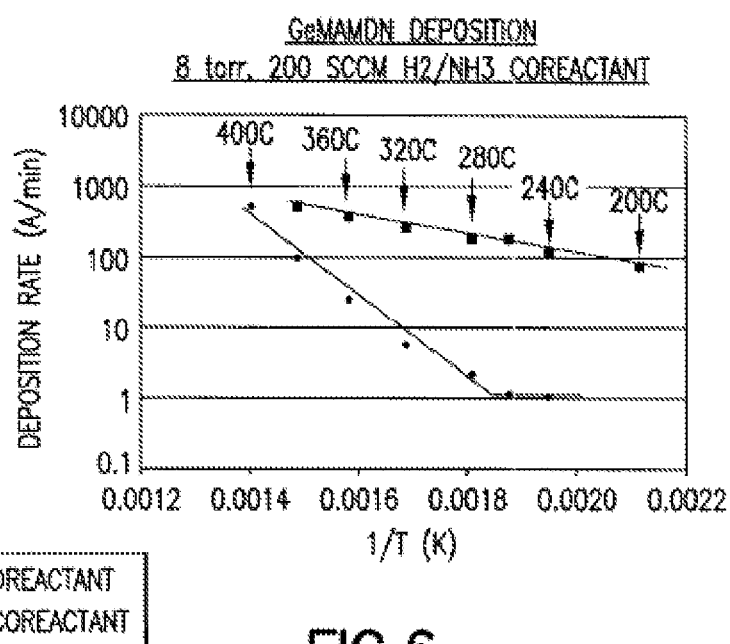
FIG. 6 is an Arrhenius plot of deposition rate, in A/min, as a function of inverse Kelvin temperature, showing the improvement in Ge deposition with ammonia co-reactant.

The invention further aspect relates to a low-temperature germanium nitride deposition process using an aminidate-based precursor, as found to be effective in forming germanium nitride at low temperature. FIG. 6 is an Arrhenius plot of deposition log rate, in A/min, as a function of 1/T, showing the improvement in Ge deposition with ammonia co-reactant for germanium methyl amidinate (GeMAMDN).

Figure 7:
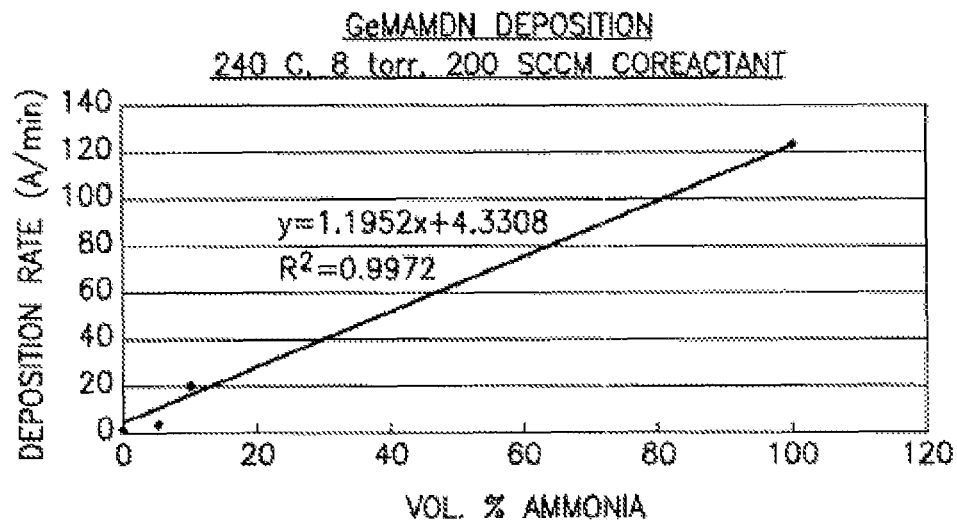
FIG. 7 is a plot of deposition rate, in A/min, as a function of volume percent ammonia introduced in the deposition operation.

With hydrogen co-reactant the precursor yields an amorphous Ge film with a deposition rate of about 2 A/min at 280° C. When the co-reactant was switched to ammonia, the deposition rate increased dramatically. A factor of 100 in deposition rate was observed at around 240° C., and a deposition rate of 75 A/min was achieved at 200° C. Furthermore, the deposited thin film turned transparent with ammonia co-reactant indicating the formation of germanium nitride. FIG. 7 shows the dominating effect of ammonia co-reactant on the deposition rate.

The invention in a further aspect relates to N, S, O-heterocyclic germanium CVD/ALD precursors for deposition of germanium metal films at low temperature. Illustrative of such precursors are [{MeC(iPrN)$_2$}$_2$Ge], [{Me$_2$N(iPr N)$_2$}$_2$Ge], [{nBuC(iPrN)$_2$}$_2$Ge], and [{MeC(NCy)$_2$}$_2$Ge]. In a specific embodiment, the precursor [{MeC(iPrN)$_2$}$_2$Ge] may be provided in a solution of toluene as a CVD precursor for germanium metal films.

In the formation of GST films, a high deposition rate, on the order of 400-500 A/min of GST alloy, and 100 A/min for Ge, along with low carbon and heteroatom impurity levels in the film, are required. Highly volatile precursors are necessary. Liquid precursors are preferred, however low melting and volatile solids may also be used with a heated bubbler system (~50° C.). Heteroatom impurities (Si, O, N) are acceptable below 10%.

The invention in such respect contemplates the use of Ge(II) and Ge(IV) precursors with the following ligands: amidinates, guanidinates, isoureates, diketonates, diketoiminates, diketiminates, carbamates, thiocarbamates, silyls, aminotroponiminate. Mixed ligand precursors are also included with combinations of the above ligands, or in combination with alkyl, dialkylamino, hydrido, or halogen groups.

The germanium precursors can be used alone to deposit metallic germanium films thermally or with a co-reactant, or with $iPr_2Te$ or other suitable tellurium precursors to deposit GeTe layers. Similarly, suitable antimony precursors may be employed to form the ternary GST alloy. Co-reactant gases/liquids usefully employed with such precursors include hydrogen, ammonia, plasma, alkylamines, silanes, and germanes.

The germanium precursors of the invention include:
(1) Ge(IV) amidinates, guanidinates, and isoureates of the formula:

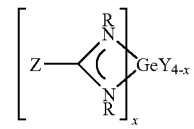

wherein each R group is independently selected from among H, $C_1$-$C_6$ alkyl, $C_3$-$C_{10}$ cycloalkyl, $C_6$-$C_{13}$ aryl, and —Si(R')$_3$ wherein each R' is independently selected from $C_1$-$C_6$ alkyl; and
each Z is independently selected from among $C_1$-$C_6$ alkoxy, —NR$_1$R$_2$, H, $C_1$-$C_6$ alkyl, $C_3$-$C_{10}$ cycloalkyl, $C_6$-$C_{13}$ aryl, and —Si(R$_4$)$_3$ wherein each R$_4$ is independently selected from $C_1$-$C_6$ alkyl;
each Y group is independently selected from among $C_1$-$C_6$ alkoxy, —NR$_1$R$_2$, and $C_1$-$C_6$ alkyl, Si(R$_4$)$_3$, and halides (Cl, Br, I), and wherein x is integer from 0 to 4;
(2) Ge beta-diketonates, diketoiminates, diketiminates of the formulae:

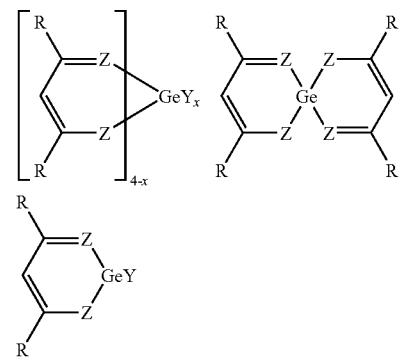

wherein each R group is independently selected from among H, $C_1$-$C_6$ alkyl, $C_3$-$C_{10}$ cycloalkyl, $C_6$-$C_{13}$ aryl, and —Si(R')$_3$; each Y group is independently selected from among $C_1$-$C_6$ alkyl, $C_6$-$C_{13}$ aryl, $C_1$-$C_6$ alkoxy, $NR_1R_2$, $Si(R_4)_3$, and halides (Cl, Br, I), x is integer from 0 to 4, Z atoms are the same or different, selected from O, S, and NR; R is selected from $C_1$-$C_6$ alkyl, $C_3$-$C_{10}$ cycloalkyl, $C_6$-$C_{13}$ aryl, $Si(R')_3$, R' is $C_1$-$C_6$ alkyl, $C_6$-$C_{13}$ aryl;

(3) Ge carbamates, thiocarbamates of the formulae:

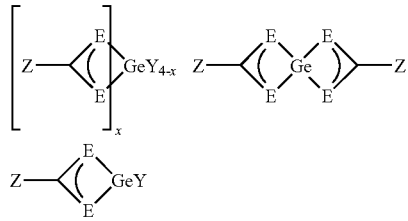

wherein each Z is independently selected from among H, $C_1$-$C_6$ alkyl, $C_3$-$C_{10}$ cycloalkyl, $C_1$-$C_6$ alkoxy, $NR_1R_2$, $C_6$-$C_{13}$ aryl, and —$Si(R_4)_3$ wherein each $R_4$ is independently selected from $C_1$-$C_6$ alkyl or aryl; each Y group is independently selected from among $C_1$-$C_6$ alkyl, $C_1$-$C_6$ alkoxy, $NR_1R_2$, $C_3$-$C_{10}$ cycloalkyl, $C_6$-$C_{13}$ aryl, $Si(R_4)_3$, and halides (Cl, Br, I), x is integer from 0 to 4, and E is either O or S;

(4) Silylgermanes of the formula:

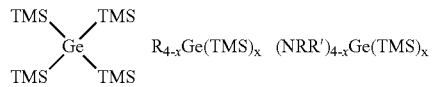

wherein TMS is $Si(R'')_3$; each R group is independently selected from among H, $C_1$-$C_6$ alkyl, $C_3$-$C_{10}$ cycloalkyl, $C_6$-$C_{12}$ aryl, and x is integer from 0 to 4;

(5) Mixed cyclopentadienyl germanes of the formulae:

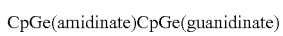

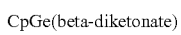

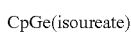

wherein each R group is independently selected from among H, $C_1$-$C_6$ alkyl, $C_3$-$C_{10}$ cycloalkyl, $C_6$-$C_{13}$ aryl, and —$Si(R')_3$ wherein each R' is independently selected from $C_1$-$C_6$ alkyl; and each Y group is independently selected from among $C_1$-$C_6$ alkyl, $C_1$-$C_6$ alkoxy, $NR_1R_2$, $C_3$-$C_{10}$ cycloalkyl, $C_6$-$C_{13}$ aryl, $Si(R_4)_3$, and halides (Cl, Br, I), x is an integer having a value of from 0 to 4, and Cp ligands may also include:

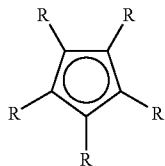

(6) Ge(II) amino-alkoxide of the formula:

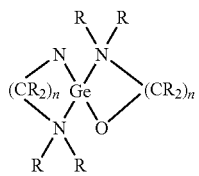

wherein each R group is independently selected from among H, $C_1$-$C_6$ alkyl, $C_3$-$C_{10}$ cycloalkyl, $C_6$-$C_{13}$ aryl, and —$Si(R')_3$, wherein each R' is independently selected from $C_1$-$C_6$ alkyl, and n is an integer having a value of from 2 to 6;

(7) Other N-heterocyclic germylenes of the formulae:

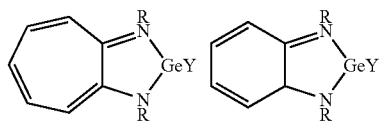

wherein each R group is independently selected from among H, $C_1$-$C_6$ alkyl, $C_3$-$C_{10}$ cycloalkyl, $C_6$-$C_{13}$ aryl, and —$Si(R')_3$, wherein each R' is independently selected from $C_1$-$C_6$ alkyl; and each Y group is independently selected from among $C_1$-$C_6$ alkoxy, $NR_1R_2$, H, $C_1$-$C_6$ alkyl, $C_3$-$C_{10}$ cycloalkyl, $C_6$-$C_{13}$ aryl, $Si(R_4)_3$, or halides (Cl, Br, I);

(8) Oxides, dithiolates, thiocarbonates of the formulae:

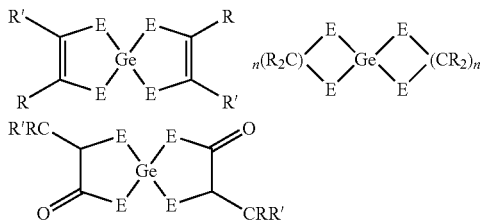

wherein each R,R' is independently selected from among $C_1$-$C_6$ alkyl, $C_3$-$C_{10}$ cycloalkyl, $C_1$-$C_6$ alkoxy, $NR_1R_2$, $C_6$-$C_{13}$ aryl, and —$Si(R_4)_3$ wherein each $R_4$ is independently selected from $C_1$-$C_6$ alkyl or aryl, and halides (Cl, Br, I), and E is either O or S.

The ALD/CVD precursors (1)-(8) described above can be prepared in liquid delivery formulations using a suitable solvent such as alkanes (e.g., hexane, heptane, octane, and pentane), aromatics (e.g., benzene or toluene), or amines (e.g., triethylamine, tert-butylamine). Precursors may also be delivered as neat liquids or as solids using a suitable solid delivery and vaporizer unit (such as the ProE-Vap™ solid delivery and vaporizer unit commercially available from ATMI, Inc., Danbury, Conn., USA).

Set out below is an identification of various specific germanium precursors of the invention.

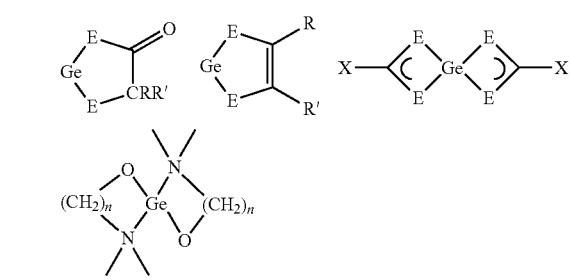

E = O, S
X = C1-C8 alkyl, fluoroalkyl, aryl, dialkylamine, alkoxy

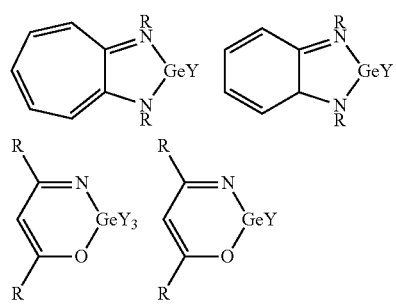

R = CH₃, tBu, CF₃
Y = alkyl, dialkylamine, H

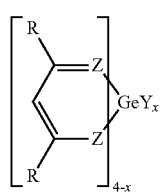

Z = N, O
R = CH₃, tBu, CF₃
Y = alkyl, dialkylamine, H

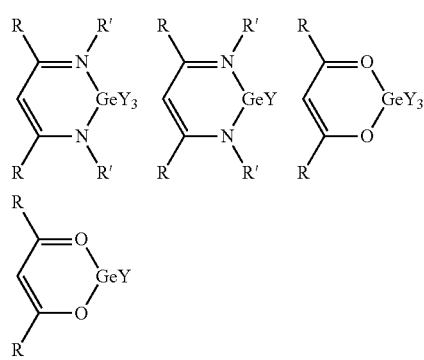

R = CH₃, tBu, CF₃
Y = alkyl, dialklyamine, H

where R = iPr, Et, t-Bu, TMS
X = dialkylamide, hydride, C1-8 alkyl
Z = dialkylamide, alkoxide, C1-8 alkyl

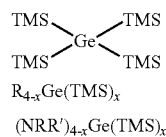

R$_{4-x}$Ge(TMS)$_x$ (NRR')$_{4-x}$Ge(TMS)$_x$

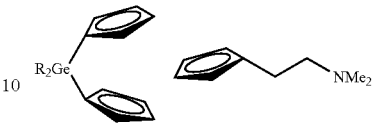

-continued

R$_{4-x}$GeCp$_x$     RGeCp (RR'N)$_{4-x}$GeCp$_x$     RR'NGeCp where Cp represents Cp, Cp*, and other C1-C6 alkyl substituted cyclopentadienyl ligands, and includes ansa-bridged germanes and alkyl(dialkylamines) [examples shown below].

Ge CVD/ALD Precursors

Ge(IV) Precursors

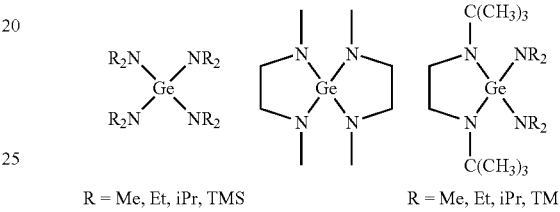

R = Me, Et, iPr, TMS         R = Me, Et, iPr, TMS

Ge(II) Precursors

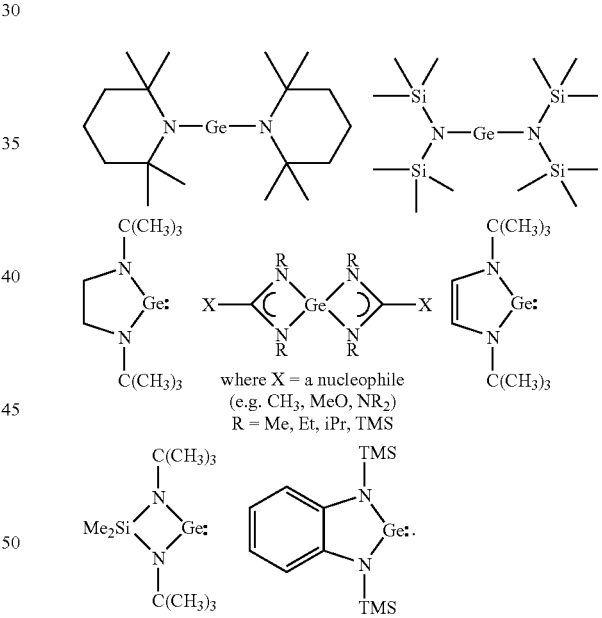

where X = a nucleophile (e.g. CH₃, MeO, NR₂)
R = Me, Et, iPr, TMS

The invention in a further aspect contemplates various metal silylamides useful for CVD and ALD deposition of thin films.

This aspect of the invention encompasses the synthesis and characterization of a class of metal precursors with disilyazacycloalkyl ligand: R5nM{N[(R₁R₂)Si(CH₂)$_m$Si(R₃R₄)]} ox-n; metal silylamides particularly with asymmetric elements in the silylamido ligands, R5nM{R4N[Si(R1R2R3)]} ox-n; carbodiimido insertion reaction with those silylamides to yield the corresponding guanidinate complexes, which can also be used as CVD/ALD precursors.

The "oligomers" of the above-discussed monomers with the same empirical formula include [R5nM{N[(R1R2)Si (CH2)mSi(R3R4)]}ox–n]x or [R5nM{R4N[Si(R1R2R3)]}ox–n]x where x is an integer having a value of 2, 3, etc.

The invention also contemplates precursors with open-structured silazane ligands in which at least one of the R5 has a functional group such as amido, alkoxyl, siloxyl and thienyl: R5nM{(R4R5R6)SiN[Si(R1R2R3)]}ox–n, and its corresponding guanidinates.

The "oligomers" of the above-discussed monomer with the same emprical formula include [R5nM{(R4R5R6)SiN[Si(R1R2R3)]}ox–n]x where x is an integer having a value of 2, 3, etc.

Each of R1, R2, R3, R4, R6 and R7 in the about formulae is independently selected from among H, C1-C6 alkyl, C3-C10 cycloalkyl, C6-C10 aryl, —Si(R8)3 and—Ge(R8)3 wherein each R8 is independently selected from C1-C6 alkyl; and —Si(R9)3 wherein each R9 is independently selected from C1-C6 alkyl; when suitable, pendant ligands attached to the above-mentioned R1, R2, R3, R4, R6 and R7 include functional group(s) providing further coordination to the metal center, such as, for example, aminoalkyl, alkoxyalkyl, aryloxyalkyl, imidoalkyl, and acetylalkyl, wherein suitable groups in these classes include those of the following formulae:

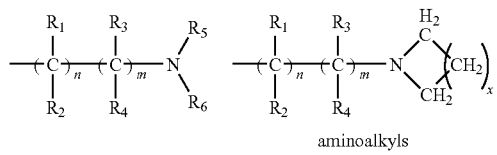

aminoalkyls wherein each of R1-R4 is the same as or different from one another, with each being independently selected from among hydrogen and C1-C6 alkyl; each of R5 and R6 is the same as or different from the other, with each being independently selected from among C1-C6 alkyl; n and m are each selected independently from 0 to 4 with the provision that m and n cannot be 0 at the same time, and x is selected from 1 to 5;

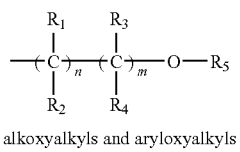

alkoxyalkyls and aryloxyalkyls wherein each of R1-R4 is the same as or different from one another, with each being independently selected from among hydrogen, C1-C6 alkyl, and C6-C10 aryl; R5 is selected from among C1-C6 alkyl, and C6-C10 aryl; and n and m are selected independently from 0 to 4, with the provision that m and n cannot be 0 at the same time.

In the metal precursors, each R5 can be independently selected from among H, C1-C6 alkyl, C3-C6 cycloalkyl, C1-C6 alkoxy, —NR1R2, and —C(R3)3, —Si(R8)3 and—Ge(R8)3 wherein each R3 is independently selected from C1-C6 alkyl; and each of R8 and R8 is independently selected from H, C1-C6 alkyl, C5-C10 cycloalkyl, C6-C10 aryl, and —Si(R9)3 wherein each R4 is independently selected from C1-C6 alkyl.

In such metal precursors, M can be any of the metals mentioned above (Ta, V, Ti, Nb, Pb, Ni, W, Ca, Ba, In, Y, La, Zr, Hf, Ir, Ru, Pt, Cr, Mo, Ge; Al, Si, Ga, Sc, V, Cr, Fe, Sb, lanthanides, Mn, Co, Ni, Zn, Cd, Te, Hg, Au, Cu, Ag, Sr, Ru) but not limited to them only; OX is the allowed oxidation state of the metal M; n is an integer having a value of from 0 to ox; and X is halogen.

The above-described precursor materials can be used as low temperature deposition precursors with reducing co-reactants such as hydrogen, H2/plasma, amines, imines, hydrazines, silanes, silyl chalcogenides such as (Me3Si)2Te, germanes such as GeH4, ammonia, alkanes, alkenes, amidines, guanidines, boranes and their derivatives/adducts and alkynes. The precursors may be employed in liquid delivery formulations, and the precursors that are liquids may be used in neat liquid form, with liquid or solid precursors being employed as desired in suitable solvents including alkane solvents (e.g., hexane, heptane, octane, and pentane), aryl solvents (e.g., benzene or toluene), amines (e.g., triethylamine, tert-butylamine), imines, guanidines, amidines and hydrazines.

The utility of specific solvent compositions for particular precursors may be readily empirically determined, to select an appropriate single component or multiple component solvent medium for liquid delivery vaporization. Solid delivery systems may be employed, of the type previously described herein.

The above-described precursors are variously shown below.

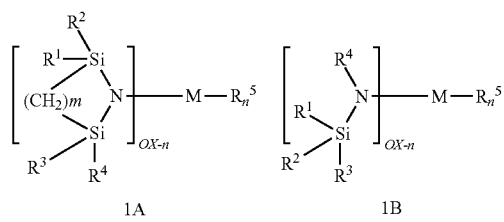

1A        1B 1A (or 1B)  +  R6N=C=NR7

-continued

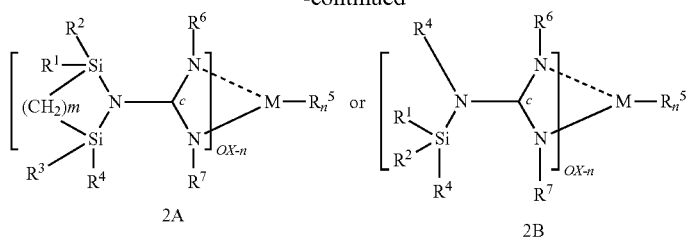

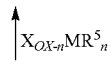

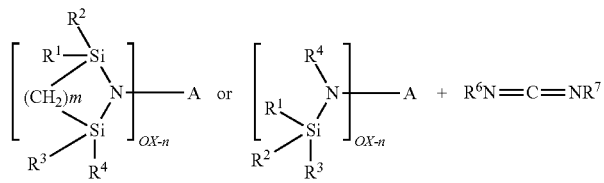

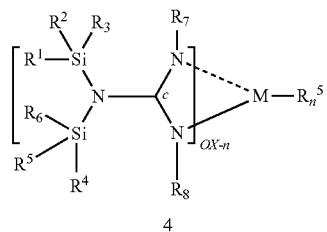

3 + R⁸N=C=NR⁷

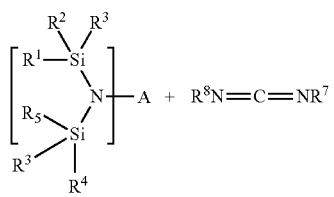

A is alkali metals

The invention in a further aspect relates to tetraalkylguanidinate and ketiminate complexes useful as CVD and ALD precursors, including a class of metal precursors with tetraalkylguanidine ligand, e.g., in the coordination mode $(R5)_nM\{N=C[(NR1R2)(NR3R4)]\}_{ox-n}$ and the semi-labile coordination mode. Under special circumstances, both coordination modes could theoretically co-exist.

All of such complexes can be synthesized from the corresponding alkali metal salts with metal halides or alkyls or mixed halides/alkyls/amides or from the direct reactions between tetraalkylguanidine with metal halides with the presence of HX absorbents such as NEt3.

The "oligomers" of such monomer with the same emprical formula include [(R5)nM{N═C[(NR1R2)(NR3R4)]}ox-n]x, where x is an integer having the value of 2, 3, etc.

Four illustrative Ge (IV) precursors have been synthesized and characterized. All of them showed promising thermal behavior and TMG2Ge(NMe2)2 is a viscous liquid at room temperature.

The invention also contemplates the corresponding guanidinate complexes R5nM{R6NC{N═C[(NR1R2)(NR3R4)]}NR7}ox-n. The "oligomers" of such monomer with the same empirical formula include [R5nM{R6NC{N═C[(NR1R2)(NR3R4)]}NR7}ox-n]x, where x is an integer having the value of 2, 3, etc.

The invention further encompasses a tetraalkylguanidine insertion reaction with metal amides to yield the corresponding guanidinate complexes, which can also be used as CVD/ALD precursors, as well as ketiminates of the formula (R5)nM{N═C[(R1R2)]}ox-n and its corresponding guanidinate complexes of the formula R5nM{R6NC[N═C(R1R2)]NR7}ox-n. The "oligomers" such monomer with the same emprical formula include [R5nM{R6NC[N═C(R1R2)]NR7}ox-n]x, where x is an integer having the value of 2, 3, etc.

In the metal complexes described above, each of R1, R2, R3, R4, R6 and R7 is independently selected from among H, C1-C6 alkyl, C3-C10 cycloalkyl, C6-C10 aryl, —Si(R8)3 and—Ge(R8)3 wherein each R8 is independently selected from C1-C6 alkyl; and —Si(R9)3 wherein each R9 is independently selected from C1-C6 alkyl; when suitable, pendant ligands attached to the above-mentioned R1, R2, R3, R4, R6 and R7 including functional group(s) providing further coordination to the metal center, such as, for example, aminoalkyl, alkoxyalkyl, aryloxyalkyl, imidoalkyl, and acetylalkyl, wherein suitable groups in these classes include those of the following formula:

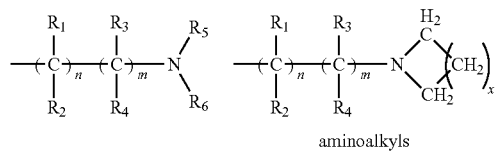

aminoalkyls wherein each of R1-R4 is the same as or different from one another, with each being independently selected from among hydrogen and C1-C6 alkyl; each of R5 and R6 is the same as or different from the other, with each being independently selected from among C1-C6 alkyl; n and m are each selected independently from 0 to 4 with the provision that m and n cannot be 0 at the same time, and x is selected from 1 to 5;

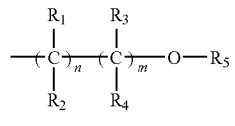

alkoxyalkyls and aryloxyalkyls wherein each of R1-R4 is the same as or different from one another, with each being independently selected from among hydrogen, C1-C6 alkyl, and C6-C10 aryl; R5 is selected from among C1-C6 alkyl, and C6-C10 aryl; and n and m are selected independently from 0 to 4, with the provision that m and n cannot be 0 at the same time.

In the metal precursors, each R5 can be independently selected from among H, C1-C6 alkyl, C3-C6 cycloalkyl, C1-C6 alkoxy, —NR1R2, and —C(R3)3, —Si(R8)3 and—Ge(R8)3 wherein each R3 is independently selected from C1-C6 alkyl; and each of R8 and R8 is independently selected from H, C1-C6 alkyl, C5-C10 cycloalkyl, C6-C10 aryl, and —Si(R9)3 wherein each R4 is independently selected from C1-C6 alkyl.

In such metal precursors, M can be any of the metals mentioned above (Ta, V, Ti, Nb, Pb, Ni, W, Ca, Ba, In, Y, La, Zr, Hf, Ir, Ru, Pt, Cr, Mo, Ge; Al, Si, Ga, Sc, V, Cr, Fe, Sb, lanthanides, Mn, Co, Ni, Zn, Cd, Te, Hg, Au, Cu, Ag, Sr, Ru) but not limited to them only; OX is the allowed oxidation state of the metal M; n is an integer having a value of from 0 to ox; and X is halogen.

The above-described precursor materials can be used as low temperature deposition precursors with reducing co-reactants such as hydrogen, H2/plasma, amines, imines, hydrazines, silanes, silyl chalcogenides such as (Me3Si)2Te, germanes such as GeH4, ammonia, alkanes, alkenes, amidines, guanidines, boranes and their derivatives/adducts and alkynes. The precursors may be employed in liquid delivery formulations, and the precursors that are liquids may be used in neat liquid form, with liquid or solid precursors being employed as desired in suitable solvents including alkane solvents (e.g., hexane, heptane, octane, and pentane), aryl solvents (e.g., benzene or toluene), amines (e.g., triethylamine, tert-butylamine), imines, guanidines, amidines and hydrazines.

The utility of specific solvent compositions for particular precursors may be readily empirically determined, to select an appropriate single component or multiple component solvent medium for liquid delivery vaporization. Solid delivery systems may be employed, of the type previously described herein.

The above-described precursors are variously shown below.

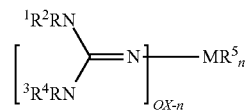

1A

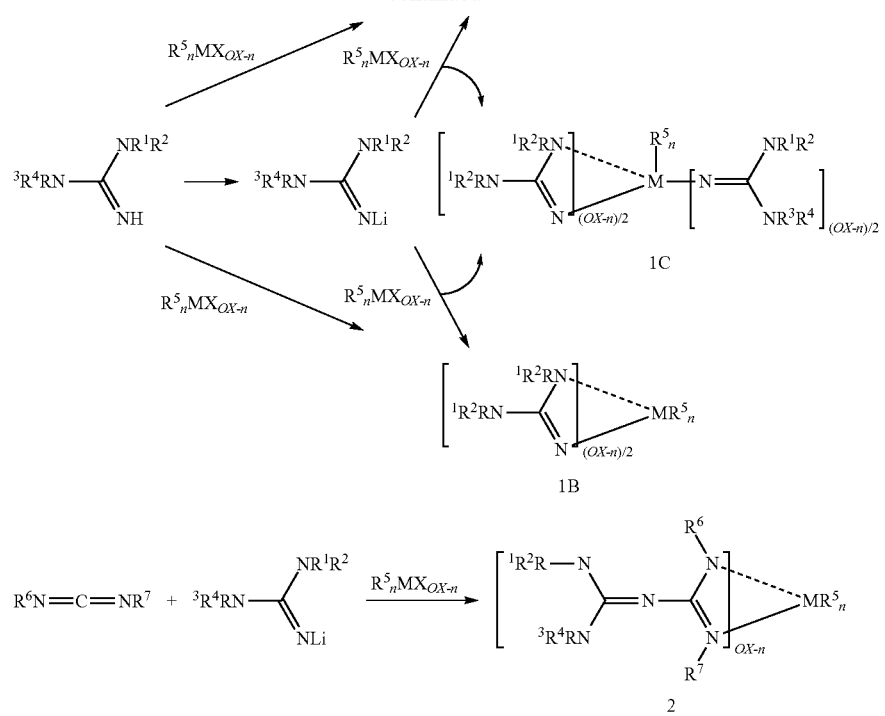
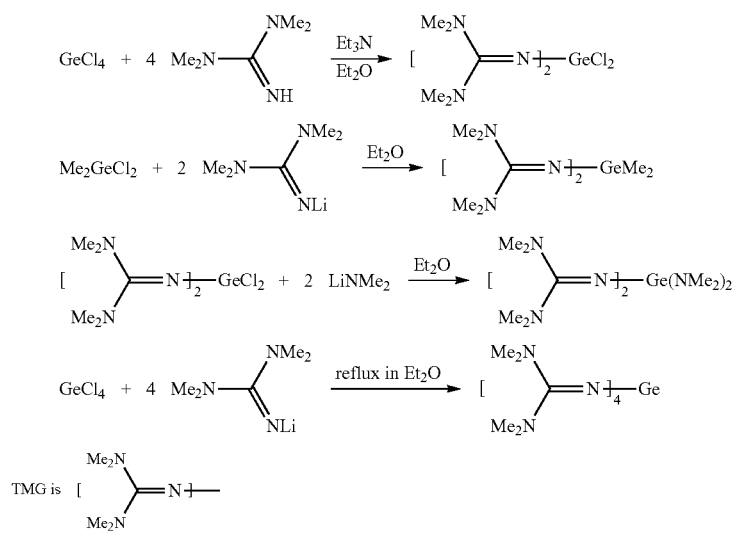
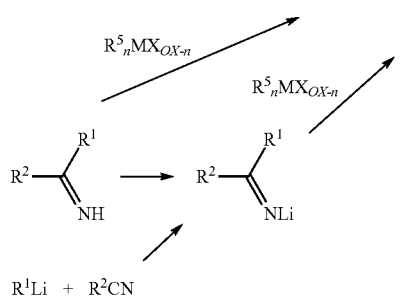

-continued

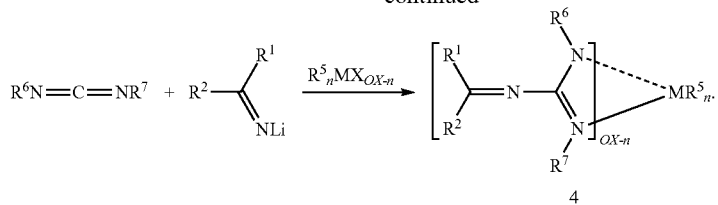

Thermal and elemental analysis is set out in the table below, for the four illustrated precursors previously mentioned as having been characterized.

| Precursor | STA | | Elemental analysis | | | Note |
|---|---|---|---|---|---|---|
| | T$_{50}$ (° C.) | Residue (%) | C (%) | H (%) | N (%) | |
| GeTMG$_2$Cl$_2$ | 230 | 3.2 | Calc. 32.29 Found 31.12 | 6.51 6.29 | 22.6 21.69 | NMR |
| GeTMG$_2$Me$_2$ | 182 | 1.0 | Calc. Found | | | NMR |
| GeTMG$_2$(NMe$_2$)$_2$ (liquid at R.T.) | 219 | 2.9 | Calc. Found | | | NMR |
| GeTMG$_4$ | 255 | 1.1 | Calc. Found | | | NMR, X-ray |

The above-described precursors are variously shown below.

The invention in a further aspect relates to dianionic chelate guanidinate ligands useful for CVD and ALD, and includes a class of metal precursors with dianionic chelate guanidine ligands of the formula (R4)nM{(R1)N═C[(NR2)(NR3)]}(ox-n)/2.

All of such precursors can be synthesized from the corresponding alkali metal salts with metal halides or alkyls or mixed halides/alkyls or from direct reactions between guanidines with metal halides with the presence of HX absorbents such as NEt3. The syntheses of the guanidinate ligands can be done from the corresponding carbodiimides and primary amines.

The "oligomers" of the above-claimed monomer with the same emprical formula include [(R4)nM{(R1)N═C[(NR2)(NR3)]}(ox-n)/2]x, where x is an integer having the value of 2, 3, etc., wherein each R1, R2, R3, R4, is independently selected from among H, C1-C6 alkyl, C3-C10 cycloalkyl, C6-C10 aryl, —Si(R5)3 and—Ge(R5)3 wherein each R8 is independently selected from C1-C6 alkyl; and —Si(R6)3 wherein each R9 is independently selected from C1-C6 alkyl; and when suitable, pendant ligands attached to the above-mentioned R1, R2, R3, R4 including functional group(s) providing further coordination to the metal center, such as, for example, aminoalkyl, alkoxyalkyl, aryloxyalkyl, imidoalkyl, and acetylalkyl, wherein suitable groups in these classes include those of the following formula:

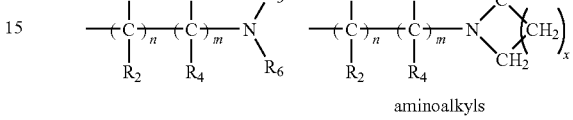

aminoalkyls wherein each of R1-R4 is the same as or different from one another, with each being independently selected from among hydrogen and C1-C6 alkyl; each of R5 and R6 is the same as or different from the other, with each being independently selected from among C1-C6 alkyl; n and m are each selected independently from 0 to 4 with the provision that m and n cannot be 0 at the same time, and x is selected from 1 to 5;

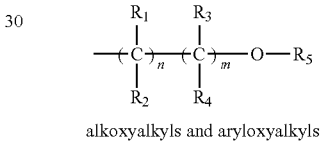

alkoxyalkyls and aryloxyalkyls wherein each of R1-R4 is the same as or different from one another, with each being independently selected from among hydrogen, C1-C6 alkyl, and C6-C10 aryl; R5 is selected from among C1-C6 alkyl, and C6-C10 aryl; and n and m are selected independently from 0 to 4, with the provision that m and n cannot be 0 at the same time.

In the metal precursors, each R5 can be independently selected from among H, C1-C6 alkyl, C3-C6 cycloalkyl, C1-C6 alkoxy, —NR1R2, and —C(R3)3, —Si(R8)3 and —Ge(R8)3 wherein each R3 is independently selected from C1-C6 alkyl; and each of R8 and R8 is independently selected from H, C1-C6 alkyl, C5-C10 cycloalkyl, C6-C10 aryl, and —Si(R9)3 wherein each R4 is independently selected from C1-C6 alkyl.

In such metal precursors, M can be any of the metals mentioned above (Ta, V, Ti, Nb, Pb, Ni, W, Ca, Ba, In, Y, La, Zr, Hf, Ir, Ru, Pt, Cr, Mo, Ge; Al, Si, Ga, Sc, V, Cr, Fe, Sb, lanthanides, Mn, Co, Ni, Zn, Cd, Te, Hg, Au, Cu, Ag, Sr, Ru) but not limited to them only; OX is the allowed oxidation state of the metal M; n is an integer having a value of from 0 to ox; and X is halogen.

The above-described precursor materials can be used as low temperature deposition precursors with reducing co-reactants such as hydrogen, H2/plasma, amines, imines, hydrazines, silanes, silyl chalcogenides such as (Me3Si)2Te, germanes such as GeH4, ammonia, alkanes, alkenes, amidines, guanidines, boranes and their derivatives/adducts and alkynes. The precursors may be employed in liquid delivery formulations, and the precursors that are liquids may be used in neat liquid form, with liquid or solid precursors being employed as desired in suitable solvents including alkane solvents (e.g., hexane, heptane, octane, and pentane), aryl solvents (e.g., benzene or toluene), amines (e.g., triethylamine, tert-butylamine), imines, guanidines, amidines and hydrazines.

The utility of specific solvent compositions for particular precursors may be readily empirically determined, to select an appropriate single component or multiple component solvent medium for liquid delivery vaporization. Solid delivery systems may be employed, of the type previously described herein.

The above-described precursors are variously shown below.

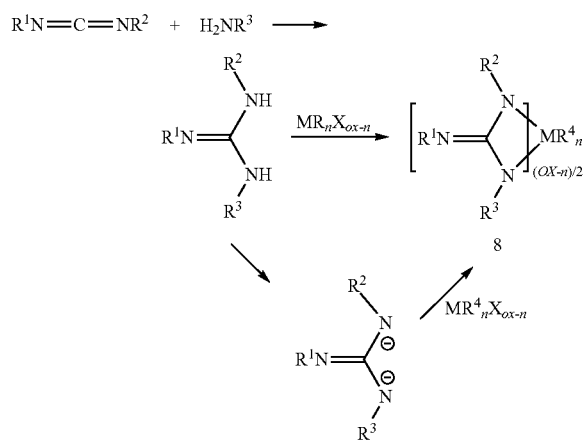

A is akali metals, X is halogens and ox is the allowed oxidation state of M.

An exemplary ligand PriN=C(PriNH)2 was synthesized and characterized as follows.

Example

To a 250 mL flask charged with 12.6 g PriNCNPri (0.1 mol) and 100 ml toluene, 5.9 g PriNH2 (0.1 mol) was added at 0° C. gradually. The resulting mixture was then refluxed at 100° C. overnight. After work-up, 11.5 g solid PriN=C(PriNH)2 was obtained. (62% yield) Anal. Calcd for C10H23N3: C, 64.81%; H, 12.51%; N, 22.68%. Found: C, 64.73%; H, 12.39%; N, 22.48%.

Selected Bond Lengths: [Å]

| C(1)—N(3) | 1.287(3) |
|---|---|
| C(1)—N(2) | 1.358(3) |
| C(1)—N(1) | 1.378(3) |

The invention in a further aspect relates to a highly selective germanium deposition process. Although discussed herein with primary reference to germanium, this process has applicability to other film deposition applications in which the film deposition process is dependent on nucleation processes, e.g., ruthenium deposition.

Phase Change Memory (PCM) is currently considered the leading contender for non-volatile memory based on its potential to scale down for several generations. Integrated GST based PCM devices have been made in the form of a large, flat layer with "plug" electrodes. Metalorganic Chemical Vapor Deposition (MOCVD) processes are under development for making these films, as it will certainly be necessary to deposit them in 3D geometries as device geometries shrink. In future generations, it will be necessary to scale this operation down to make the entire phase change chalcogenide section a plug within a via of insulating material such as silicon oxide, silicon nitride or low k dielectric.

Figure 8:
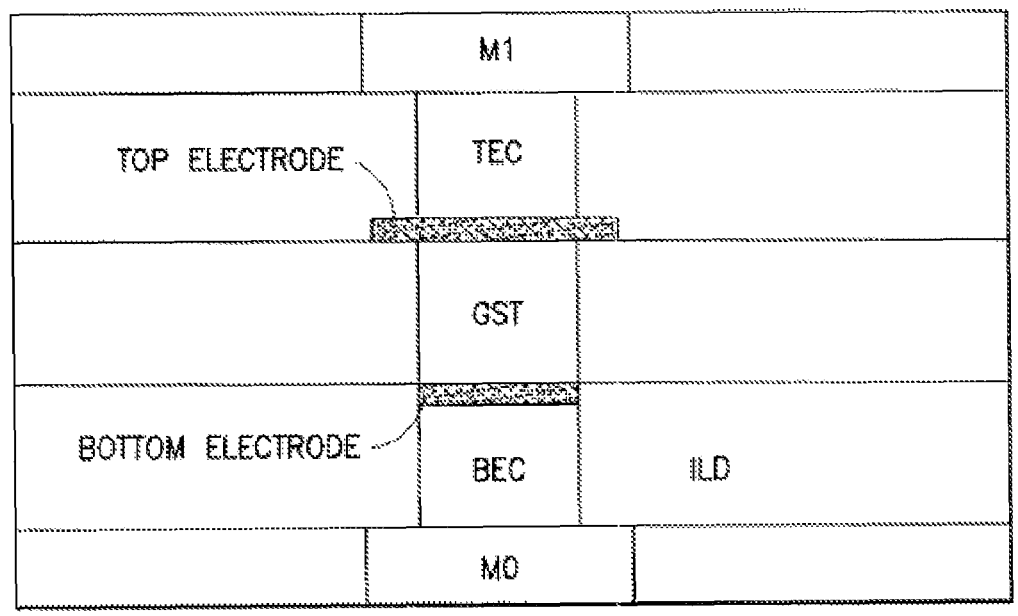
FIG. 8 is a schematic representation of a schematic of a GST device structure.

An example of this can be seen in FIG. 8, which is a schematic of a GST device structure showing the GST plug, top electrode, bottom electrode, interlayer dielectric and associated layers of the device. Since neither etching nor CMP of this material is well established, making such a plug is not trivial, since a fairly thick layer is needed in order to allow for the bulk phase change that stores information in the form of a resistivity change. It would be desirable to grow the material in a "bottom up" way only in the via, without coating the rest of the structure. In order for this to occur, the deposition process must be highly selective, growing quickly on the desired surfaces and slowly or not at all on others.

It might also be desirable to have the PCM material have poor contact with sidewalls of the via so as to reduce thermal contact and crosstalk between adjacent cells. Thus it could be desirable to have different sticking coefficients and nucleation likelihood on different surfaces.

It is also necessary to develop low temperature MOCVD processes for making these films, at temperatures of 300° C. or less, since some components are volatile enough that stoichiometry control becomes difficult above this temperature.

During our investigations of Ge precursors for PCMs, an amide-based precursor was discovered that has very strong selectivity based on surface state of the substrate on which it is being grown. This precursor, Ge(NMe2)4, undergoes a deposition rate change of close to 1000× over an extremely narrow temperature range, just 10-15° C. This is virtually unique behavior and we are aware of no other compound that does this.

For such a strong effect to be taking place, it seemed likely that it was due to changes in the deposition surface and some kind of autocatalysis. These films were deposited on TiN, which was purchased commercially more than a year previously and cleaved into pieces for these experiments. Ti and TiN rapidly form oxides from exposure to atmosphere, and there is little doubt that the nucleation surface as inserted into the reactor was some form of Ti oxide or oxide nitride mix. Ti changes between various suboxides such as TiO2 and Ti2O3 readily, however, so it is possible that under reducing conditions such as the forming gas which flows through the reactor during heatup on the substrate, or even the hydrogen in which deposition takes place, the surface is altered in a fairly abrupt way at a particular transition temperature. Heatup from room temperature was fixed at 4 minutes in all experiments. This could explain the behavior observed above, with deposition rate increasing from a few A/min up to 1000 A/min in a 10-15 degree C. window, and with the location of this window shiftable by tens of degrees based on the reactant gas and partial pressure of the gases present.

In order to test this theory, deposition was carried out on SiO2 substrates, and on a piece of TiN which was first heated to 400 C in 8T of hydrogen before being cooled to deposition temperature over the course of 10 minutes. The results included a deposition rate at 280 C of about 3 A/min deposited on TiN that had been exposed to air then placed on a susceptor. On a SiO2 substrate, the deposition rate was closer to 0.3 A/min, an order of magnitude lower. Meanwhile, on the substrate which was preheated to 400 C then cooled in a reducing atmosphere in the reactor, deposition rate was close to 600 A/min at 280 C, and the rate was substantially higher at low temperatures. The preheated substrate was the closest simulation of a standard manufacturing process, where a TiN or similar electrode would be deposited in one part of a cluster tool, after which the substrate would be transferred to the CVD deposition module without any air exposure. The 200:1 ratio between deposition rates on preheated TiN and SiO2 is sufficient to obtain a very high selectivity on any combination of surfaces like this one. It is expected that this ratio would increase still further with clean, "in situ" deposited TiN and SiO2.

The most straightforward potential benefit to the unique behavior of this precursor was bottom up fill of the vias to make a plug of chalcogenide phase change memory material. The Ge initial layer can be used as a somewhat more favorable growth site for a complete suite of precursors to help prevent "seams" or voids in the plug.

If it were desirable, it might also be possible to have a plug of PCM material with poor contact to the side walls, providing better thermal isolation and less cross talk between adjacent PCM cells. Slow deposition and poor nucleation may lead to a poorly adhering layer with pores near the surface.

A more indirect benefit is creation of a semiconductor compatible nucleation surface for other nucleation sensitive materials. For example, it is well known that Ru metal is difficult to grow in a purely reducing atmosphere; it tends to need some oxygen in its vicinity, for most CVD precursors. In addition, it is very hard to deposit it uniformly on a SiO2 surface. This Ge precursor can be used to form a nucleation layer on Si at the bottom of a trench or via so that a slightly oxidizing process can be used, since Ge does not bond as strongly to oxygen as Si does, or a reducing process which deposits more easily on clean metal could be used. This approach can be extended to deposition of materials other than Ru, providing they have some surface chemistry sensitivity that can be exploited.

In a more sophisticated approach, a surface, metal, nitride and/or Ge, can have its surface chemistry changed via reactant gases (for example from oxide to metal) in order to switch it on and off for purposes of deposition from this precursor. This in turn allows a chip surface that may have multiple materials exposed to have different surfaces switched on and off, depending on the layer material and coreactant, relative to Ge deposition. The Ge can then be used as a protective layer for further chemistry modifications, e.g., as a hard mask, a sacrificial layer, etc. This principle can be extended to other elements than Ge upon finding appropriate precursors with this strong sensitivity to surface and deposition temperature.

Other chemicals and chemical families that may exhibit this behavior include N-coordinated germanium amides, amidinates, guanidinates, and N-heterocyclic germylenes. The described process is also applicable to metal-organic CVD or ALD precursors comprising a metal selected from Ge, Sb, Te, Be, Mg, Ti, V, Cr, Mn, Fe, Ni, Cu, Zn, Y, Zr, Nb, Mo, Ru, Rh, Pd, Ag, Cd, Hg, La, Hf, Ta, W, Re, Os, Ir, Pt, Au, Sn, Pb, As, P, Bi, Al, Ga, In, Tl, and Si, to which is bound at least one weakly coordinating ligand selected from among halogen, B-diketiminate, nitrile, isonitrile, aminotroponiminate, carbonyl, phosphido, imido, amine, pyridine, amidinate, guanidinate, nitrosyl, silyl, stibene (R3Sb), sulfide, and cyclopentadienyl.

In a broad aspect, the present invention contemplates metal precursors of the formula $MA_yB_x$ wherein M is a metal selected from among Ge, Sb and Te, and A is a ligand selected from the group consisting of all ligands disclosed herein, and y+x equals the oxidation state on metal M.

While the invention has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A method of fabricating a microelectronic device comprising germanium, said method comprising depositing germanium on a microelectronic device substrate by a vapor deposition process including contacting the microelectronic device substrate with a precursor vapor of a germanium precursor comprising germanium bis(n-butyl, N,N-diisopropylamidinate),

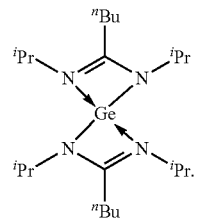

2. The method of claim 1, wherein said vapor deposition process comprises chemical vapor deposition or atomic layer deposition.

3. The method of claim 1, wherein the germanium is deposited on the microelectronic device substrate to form a germanium-containing material thereon, and the method further comprises depositing one or more of nitrogen, silicon and carbon as corresponding component(s) of the germanium-containing material.

4. The method of claim 1, further comprising depositing tellurium on the microelectronic device substrate.

5. The method of claim 4, further comprising depositing antimony on the microelectronic device substrate.

6. The method of claim 1, wherein said vapor deposition process is carried out to form an alloy of germanium-antimony-tellurium on the microelectronic device substrate.

7. The method of claim 6, wherein the method comprises forming a phase change memory cell on the microelectronic device substrate.

8. The method of claim 6, further comprising incorporating nitrogen in the alloy of germanium-antimony-tellurium.

9. The method of claim 6, further comprising incorporating silicon in the alloy of germanium-antimony-tellurium.

10. The method of claim 6, wherein the alloy of germanium-antimony-tellurium is deposited in a via on the microelectronic device substrate.

11. The method of claim 10, wherein the via is in a low k dielectric material.

12. The method of claim 10, wherein the via is in a silicon oxide material.

13. The method of claim 10, wherein the via is in a silicon nitride material.

14. The method of claim 1, where the vapor deposition process is carried out at temperature below 300° C.

15. The method of claim 6, where the vapor deposition process is carried out at temperature below 300° C.

16. The method of claim 6, wherein the germanium-antimony-tellurium alloy contains carbon.

17. The method of claim 1, wherein germanium is deposited in a via or trench on said microelectronic device substrate in said vapor deposition process.

18. The method of claim 1, wherein germanium is deposited on said microelectronic device substrate in said vapor deposition process in the presence of a co-reactant.

19. The method of claim 18, wherein said co-reactant is selected from the group consisting of hydrogen, ammonia, plasma, amines, alkanes, alkenes, amidines, guanidines, boranes and their adducts and derivatives, alkynes, alkylamines, imines, hydrazines, silanes, silyl chalcogenides, and germanes.

20. The method of claim 17, wherein said co-reactant comprises ammonia.

* * * * *

UNITED STATES PATENT AND TRADEMARK OFFICE
CERTIFICATE OF CORRECTION

PATENT NO. : 8,008,117 B2
APPLICATION NO. : 12/860906
DATED : August 30, 2011
INVENTOR(S) : William Hunks et al.

It is certified that error appears in the above-identified patent and that said Letters Patent is hereby corrected as shown below:

Cover page, Item (63): "Continuation of application No. 12/307,101, filed as application No. PCT/US2007/063830 on Mar. 12, 2007, now Pat. No. 7,838,329." should be -- Continuation of application No. 12/307,101, filed on Feb. 20 2009, now Pat. No. 7,838,329, which is a §371 of application No. PCT/US2007/063830, filed on Mar. 12, 2007. --.

Column 5, lines 14-15: "...each of $R^2$ and $R^3$ is independently selected from..." should be -- ...each of $R^1$, $R^2$ and $R^3$ is independently selected from... --.

Column 15, line 17: the reaction " 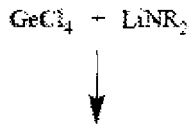 " should be followed by -- R = Me, Et, iPr, t-Bu or combinations --.

Column 32, line 65: "$GeCl_2 \cdot C_4H_5O_2$" should be -- $GeCl_2 \cdot C_4H_8O_2$ --.

Column 40, line 15: " 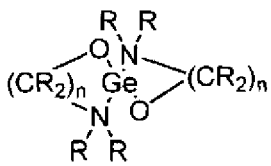 " should be -- 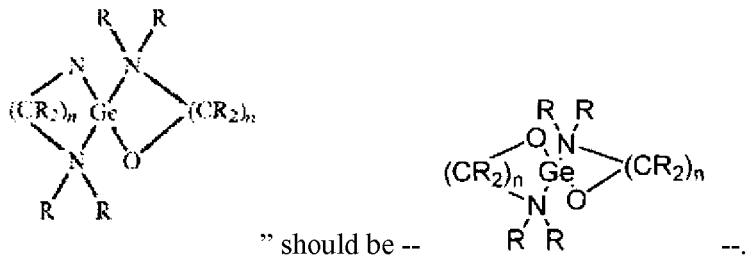 --.

Signed and Sealed this
Fourteenth Day of August, 2012

David J. Kappos
*Director of the United States Patent and Trademark Office*

CERTIFICATE OF CORRECTION (continued)
U.S. Pat. No. 8,008,117 B2

Column 45, line 1: Structure 2B " 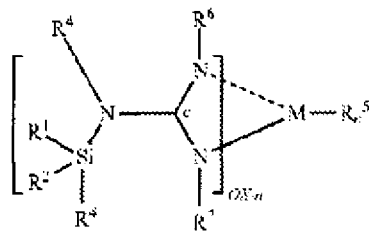 " should be 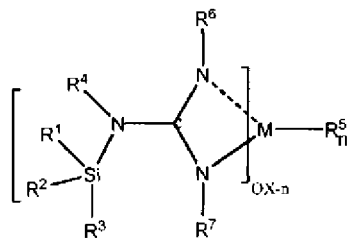 --.

Column 49, approximately line 20: Structure 1B " 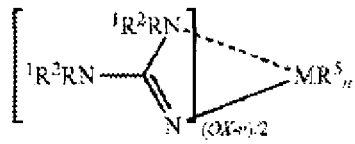 " should be 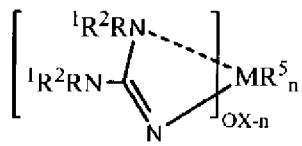 --.